US012779102B2

(12) United States Patent
Davie et al.

(10) Patent No.: US 12,779,102 B2
(45) Date of Patent: Nov. 3, 2026

(54) SOUND-ATTENUATING ENCLOSURE FOR A VACUUM SOURCE OF A WASTE COLLECTION UNIT

(71) Applicant: Stryker Corporation, Kalamazoo, MI (US)

(72) Inventors: Daniel Davie, Kalamazoo, MI (US); Michael Zollinger, Chelsea, MI (US); Brian MacLachlan, Norton Shores, MI (US)

(73) Assignee: Stryker Corporation, Portage, MI (US)

( * ) Notice: Subject to any disclaimer, the term of this patent is extended or adjusted under 35 U.S.C. 154(b) by 411 days.

(21) Appl. No.: 17/500,483

(22) Filed: Oct. 13, 2021

(65) Prior Publication Data

US 2022/0031929 A1 Feb. 3, 2022

Related U.S. Application Data

(63) Continuation of application No. 16/065,440, filed as application No. PCT/US2016/067812 on Dec. 20, 2016, now Pat. No. 11,160,909.

(Continued)

(51) Int. Cl.
*A61M 1/00* (2006.01)

(52) U.S. Cl.
CPC ................ *A61M 1/63* (2021.05); *A61M 1/60* (2021.05); *A61M 1/65* (2021.05); *A61M 1/71* (2021.05);

(Continued)

(58) Field of Classification Search
CPC ............ A61M 1/63; A61M 1/60; A61M 1/65; A61M 1/71; A61M 1/72; A61M 1/77;

(Continued)

(56) References Cited

U.S. PATENT DOCUMENTS

| | | | |
|---|---|---|---|
| 3,457,645 | A | 7/1969 | Swanson |
| 3,599,871 | A | 8/1971 | Ruppel et al. |

(Continued)

FOREIGN PATENT DOCUMENTS

| | | | |
|---|---|---|---|
| CA | 2545607 | A1 | 10/1999 |
| EP | 2044964 | A2 | 4/2009 |
| WO | 03075821 | A2 | 9/2003 |

OTHER PUBLICATIONS

International Search Report for Application No. PCT/US2016/067812 dated Apr. 26, 2017, 6 pages.

*Primary Examiner* — Guy K Townsend
*Assistant Examiner* — Alessandro R Del Priore
(74) *Attorney, Agent, or Firm* — Howard & Howard Attorneys PLLC

(57) ABSTRACT

A waste collection unit including a waste container, and vacuum source to collect medical waste into the waste container. The vacuum source is disposed within a sound attenuating enclosure that defines an enclosure inlet for receiving cooling air and an enclosure outlet for discharging warmed cooling air. The sound attenuating enclosure is at least partially formed of a sound-absorbing material and may define a pocket for receiving a first end of the vacuum source. The first end of the vacuum source may engage a seat of the sound attenuating enclosure to provide a cooling air barrier. The seat may define a bottom portion of the pocket. Internal geometries of the sound attenuating enclosure may be shaped to define another air path that does not pass through the vacuum source. A plenum may be attached to the sound attenuating enclosure and define a plenum chamber to collect the warmed cooling air.

16 Claims, 31 Drawing Sheets

Related U.S. Application Data

(60) Provisional application No. 62/387,394, filed on Dec. 24, 2015.

(52) U.S. Cl.
CPC ................ *A61M 1/72* (2021.05); *A61M 1/77* (2021.05); *A61M 1/80* (2021.05); *A61M 1/88* (2021.05); *A61M 2205/07* (2013.01); *A61M 2205/3606* (2013.01); *A61M 2205/362* (2013.01); *A61M 2205/42* (2013.01); *A61M 2209/10* (2013.01)

(58) Field of Classification Search
CPC ...... A61M 1/80; A61M 1/88; A61M 2205/07; A61M 2205/3606; A61M 2205/362; A61M 2205/42; A61M 2209/10; A61M 2205/103; A61M 2209/086; A61M 1/0001; A61M 1/0023; A61M 1/0005; A61M 1/0058; A61M 1/0094
See application file for complete search history.

(56) References Cited

U.S. PATENT DOCUMENTS

| | | | | | |
|---|---|---|---|---|---|
| 4,642,128 | A | | 2/1987 | Solorzano | |
| 4,701,193 | A | | 10/1987 | Robertson et al. | |
| 4,810,269 | A | * | 3/1989 | Stackhouse | B01D 46/10<br>55/471 |
| 5,037,431 | A | | 8/1991 | Summers et al. | |
| 5,226,939 | A | | 7/1993 | Nicolas et al. | |
| 5,611,409 | A | * | 3/1997 | Arseneau | F01N 1/089<br>181/243 |
| 6,082,487 | A | * | 7/2000 | Angelo | F01N 1/04<br>181/282 |
| 6,171,072 | B1 | * | 1/2001 | West | F04B 49/06<br>417/298 |
| 6,342,048 | B1 | * | 1/2002 | Verkaart | B01D 29/908<br>604/323 |
| 7,387,264 | B2 | | 6/2008 | Kassanits | |
| 7,621,898 | B2 | | 11/2009 | Lalomia et al. | |
| 7,879,228 | B2 | | 2/2011 | Dunn et al. | |
| 9,643,196 | B2 | | 5/2017 | Klinefelter | |
| 10,105,740 | B2 | | 10/2018 | Hoffmeyer et al. | |
| 11,160,909 | B2 | | 11/2021 | Davie et al. | |
| 2005/0103339 | A1 | * | 5/2005 | Daly | A61M 16/0875<br>128/204.18 |
| 2007/0135779 | A1 | * | 6/2007 | Lalomia | A61M 1/60<br>604/319 |
| 2009/0010219 | A1 | | 1/2009 | Lee et al. | |
| 2009/0277333 | A1 | * | 11/2009 | Sakurai | C01B 13/0259<br>96/150 |
| 2010/0010477 | A1 | * | 1/2010 | Augustine | A61M 1/78<br>604/327 |
| 2011/0072771 | A1 | | 3/2011 | Palmerton et al. | |
| 2015/0027561 | A1 | | 1/2015 | Mauthe | |
| 2015/0182720 | A1 | * | 7/2015 | Taylor | B01D 53/047<br>128/205.12 |
| 2015/0224237 | A1 | | 8/2015 | Reasoner et al. | |
| 2017/0368239 | A1 | * | 12/2017 | Askem | A61M 1/982 |
| 2019/0001029 | A1 | | 1/2019 | Davie et al. | |

* cited by examiner

SOUND-ATTENUATING ENCLOSURE FOR A VACUUM SOURCE OF A WASTE COLLECTION UNIT

RELATED APPLICATION

This application is a continuation of copending U.S. application Ser. No. 16/065,440, filed Jun. 22, 2018, which is a national entry of International Application No. PCT/US2016/067812, filed Dec. 20, 2016, which claims the benefit of and priority to United States Provisional Application No. 62/387,394, filed on Dec. 24, 2015, each of which is hereby incorporated by reference in its entirety

TECHNICAL FIELD

The present disclosure relates to a waste collection unit for collecting waste materials, such as bodily fluids, generated during medical procedures carried out in a health care facility

BACKGROUND

Waste collection units are well known for use in health care facilities to collect waste material generated during medical procedures. Waste collection units comprise one or more waste containers connected to a vacuum source. One or more suction lines extend from the waste containers and are positioned near the site from which the waste material is to be collected. When the vacuum source is operating, the waste material is drawn through the suction lines into the waste containers. Often, the vacuum source utilized by the waste collection unit is an on-board vacuum pump that produces significant amounts of noise and heat during operation. The noise can be distracting to medical personnel and the heat can damage sensitive electronic controls carried by the waste collection unit.

A smoke evacuation system may also be employed by the waste collection unit. A smoke conduit is connected to the smoke evacuation system to remove smoke, such as smoke associated with electrocautery procedures. Smoke evacuation systems often comprise a smoke evacuator, such as a motor and fan assembly, to draw in air and smoke from the surgical site. The smoke evacuator, much like the vacuum pump, tends to be noisy when operating, and thus may also distract the medical personnel performing the medical procedure.

Typical waste collection units comprise a cleaning system that operates to clean internal surfaces of the waste containers being used to collect the waste material. The cleaning system may employ a sprinkler that operates similar to sprinklers in a dishwasher in which water pressure alone provides the power to rotate the sprinklers. In this case, energy that could otherwise be used for cleaning the internal surfaces is lost to rotating the sprinkler. In other cases, the sprinkler may be stationary and unable to vary a direction of cleaning spray. In certain situations, these sprinklers may not be able to suitably clean the internal surfaces of the waste containers.

There is a need in the art for a waste collection unit capable of overcoming one or more of the aforementioned problems.

SUMMARY

In one embodiment, a waste collection unit is provided for collecting waste material through a suction line during a medical procedure. The waste collection unit comprises a waste container configured to be in fluid communication with the suction line to collect the waste material during the medical procedure. The waste container defines a collection chamber and a vacuum port. A vacuum source is in selective communication with the vacuum port of the waste container for providing a vacuum in the waste container to draw the waste material into the waste container through the suction line. The vacuum source defines a vacuum passage to carry air through the vacuum source. The vacuum passage has a vacuum inlet for receiving the air and a vacuum outlet for directing the air from the vacuum source. The vacuum source is disposed in a sound attenuating enclosure. The sound attenuating enclosure defines an enclosure inlet for receiving cooling air to cool the vacuum source and an enclosure outlet for discharging warmed cooling air from the sound attenuating enclosure. The sound attenuating enclosure comprises a first section at least partially formed of a first sound-absorbing material configured to attenuate noise generated by the vacuum source during operation. The first section has an interior surface with geometric features formed therein to accommodate the vacuum source and define a cooling air path for the cooling air.

In another embodiment, a smoke evacuation system is provided for evacuating smoke through a smoke conduit during a medical procedure. The smoke evacuation system comprises a filter housing for removably receiving a filter. A smoke evacuator is configured to draw the smoke from the smoke conduit into the filter housing and through the filter. The smoke evacuator is disposed in a sound attenuating enclosure. The sound attenuating enclosure defines an enclosure inlet to receive filtered air from the filter housing and an enclosure outlet to direct the filtered air away from the sound attenuating enclosure. The sound attenuating enclosure comprises a first section at least partially formed of a sound-absorbing material configured to attenuate noise generated by the smoke evacuator during operation. The sound attenuating enclosure further defines a cooling air inlet for receiving cooling air and the first section has an interior surface with geometric features formed therein to accommodate the smoke evacuator and define a cooling air path for the cooling air.

In yet another embodiment, a waste collection unit is provided for collecting waste material through a suction line during a medical procedure. The waste collection unit comprises a waste container configured to be in fluid communication with the suction line to collect the waste material during the medical procedure. The waste container has an internal surface defining a collection chamber. A vacuum source is in selective communication with the waste container for providing a vacuum in the waste container to draw the waste material into the waste container through the suction line. A cleaning system includes a liquid delivery device rotatably supported relative to the waste container. The liquid delivery device directs liquid on the internal surface of the waste container. The cleaning system includes an actuator operatively coupled to the liquid delivery device for rotating the liquid delivery device relative to the waste container to vary a direction in which the liquid is directed on the internal surface.

DETAILED DESCRIPTION

Referring to the Figures, wherein like numerals indicate like or corresponding parts throughout the several views, a waste collection unit for collecting waste materials is shown generally at 100. The waste collection unit 100 collects waste material generated during medical procedures (e.g., surgical procedures) performed in a health care facility such as a hospital. The waste material may include bodily fluids, smoke, body tissues, irrigation liquids, and/or other materials that may be generated during various medical procedures. Often times, medical procedures require large amounts of saline and/or other irrigation liquids for irrigating an anatomical site. As a result, the waste collection unit 100 is capable of handling large amounts of waste material. The waste collection unit 100 collects the waste material for later discharge.

During use, the waste collection unit 100 collects the waste material and stores the waste material on-board until such time as a user is ready to off-load the waste material and dispose of the waste material. In the embodiments shown, the waste collection unit 100 is capable of storing waste material from a series of different medical procedures during the course of a day or across several days, without requiring off-loading of the waste material. Once the waste material either fills the waste collection unit 100, or the user is ready to dispose of the waste material, the waste collection unit 100 is transported by the user to a docking station or other disposal area. The waste material is emptied from the waste collection unit 100 to a waste drain or treatment location, and the waste collection unit 100 is cleaned for further use. In other embodiments, not shown, the waste collection unit 100 may form part of a permanent waste collection installation or the waste collection unit 100 may be intended to remain stationary during waste collection and disposal.

The waste collection unit 100 includes various features for simplifying use by health care personnel including doctors, nurses, and other users of the waste collection unit 100, and for improving patient outcomes from the various medical procedures. Some of the features were designed to reduce the noise typically experienced when operating such waste collection units, and to improve cleaning of the waste collection unit 100 between uses.

Figure 1:
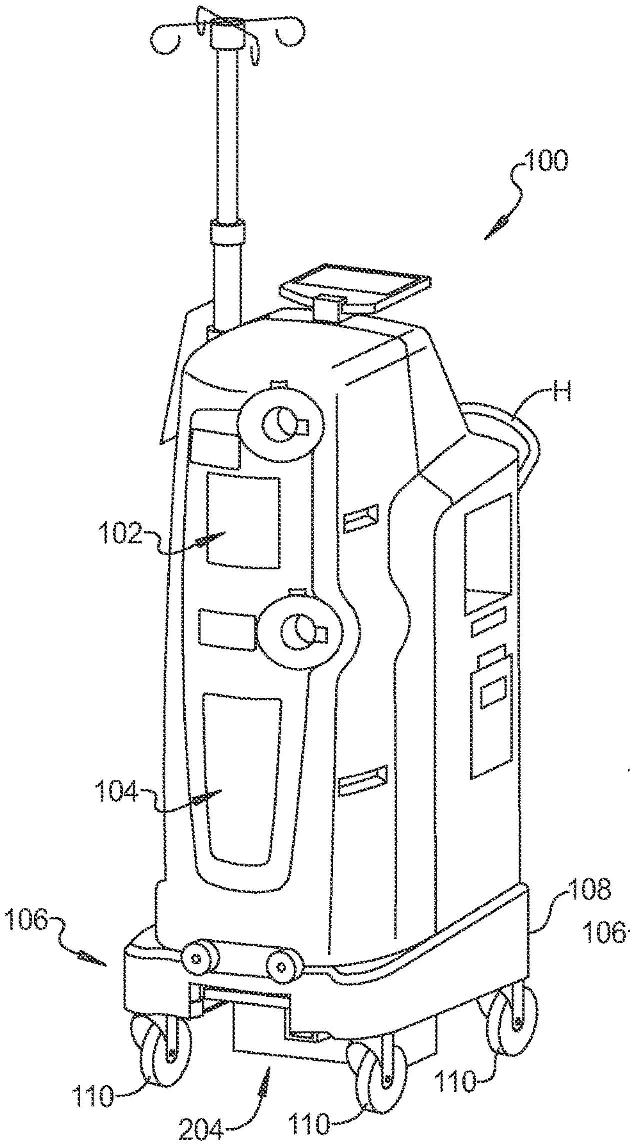
FIG. 1 is a perspective view of a waste collection unit.
Figure 2:
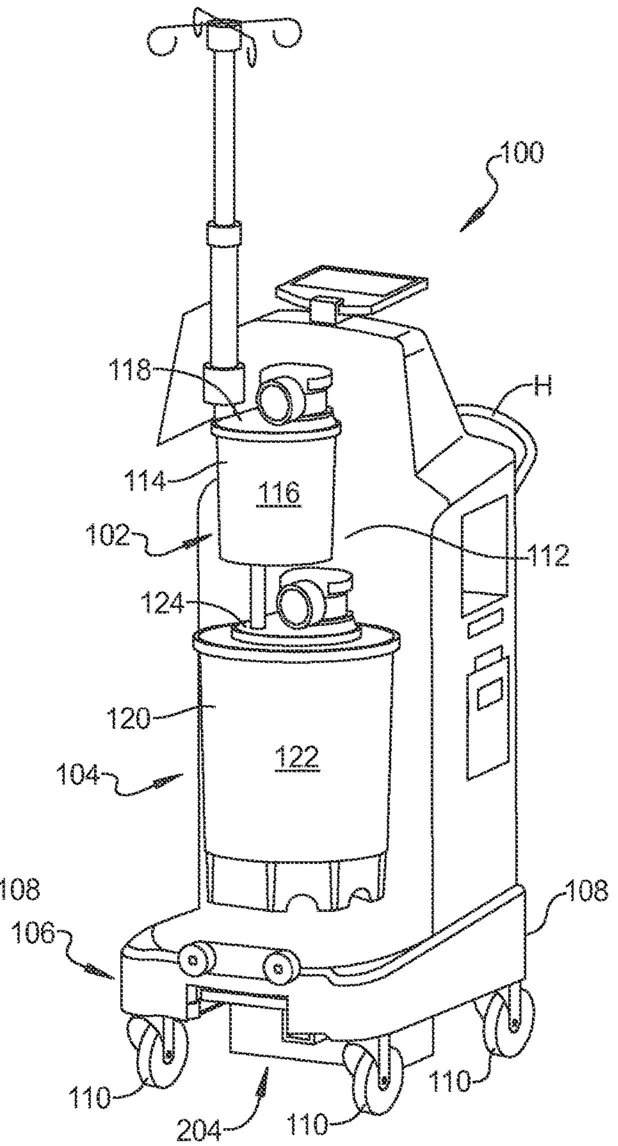
FIG. 2 is a perspective view of the waste collection unit with a cover removed.

Referring to FIGS. 1 and 2 (front cover removed in FIG. 2), the waste collection unit 100 comprises upper and lower waste containers 102, 104 to collect and temporarily store the waste material during use. A cart 106 supports the waste containers 102, 104. More specifically, the waste containers 102, 104 are stacked one above the other on the cart 106. The cart 106 includes a cart base 108 supporting the waste containers 102, 104.

A plurality of wheels 110 are mounted to a bottom of the cart base 108 to provide mobility to the cart 106. The cart 106 comprises a vertical chassis 112 fixed to the cart base 108. The vertical chassis 112 extends upwardly from the cart base 108.

One or more handles H may be mounted to the vertical chassis 112 to facilitate movement of the waste collection unit 100 between use areas, and between the use areas and the docking station. Thus, users can move the cart 106 around the health care facility to collect waste material generated during medical procedures performed in different locations throughout the health care facility. Of course, the wheels 110 and handles H may be lacking in the embodiments in which the waste collection unit 100 forms part of a permanent installation or when the waste collection unit 100 is intended to be stationary.

The upper waste container 102 comprises an upper canister 114 that is slightly frusto-conical in shape, but appears generally cylindrical. The upper canister 114 defines an upper waste chamber 116 for holding waste material. An upper cap 118 covers the upper canister 114 to close the upper waste chamber 116.

The lower waste container 104 comprises a lower canister 120 that is also slightly frusto-conical in shape. The lower canister 120 defines a lower waste chamber 122 for holding waste material. A lower cap 124 covers the lower canister 120 to close the lower waste chamber 122. The canisters 114, 120 may assume any shape that is suitable for containing the waste material. The canisters 114, 120 are shown in a stacked configuration, but may be placed side-by-side on the cart 106 in other embodiments. Additionally, the canisters 114, 120 may be the same size or different sizes, or fewer or additional canisters (not shown) could be employed. The canisters 114, 120 may be formed of glass, suitable plastic materials, or other materials.

Figure 3:
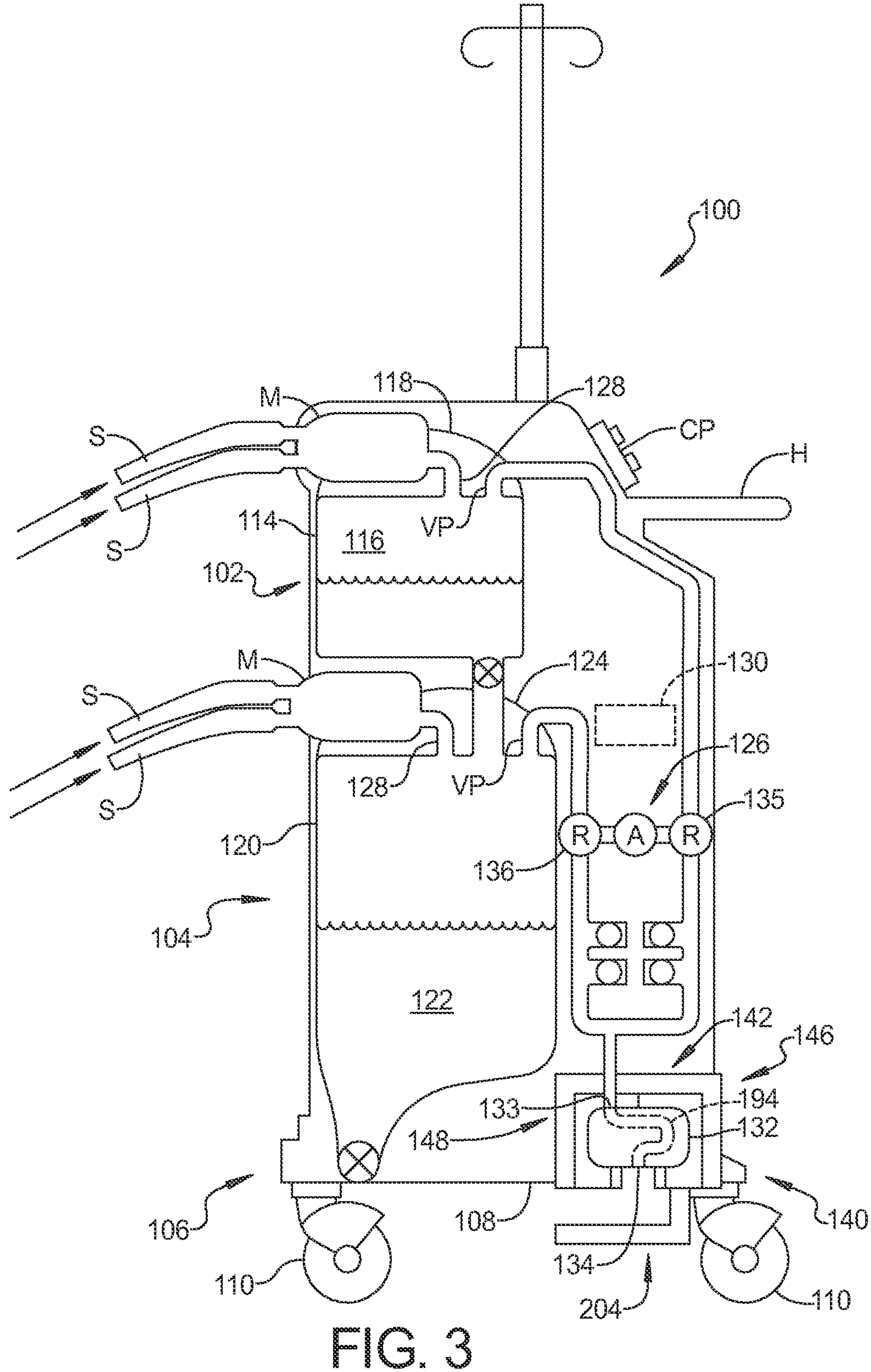
FIG. 3 is a schematic illustration of a vacuum circuit of the waste collection unit.

Referring to FIG. 3, a schematic representation of waste material being collected by the waste collection unit 100 is shown. A vacuum is pulled in each of the waste containers 102, 104 with a vacuum circuit 126, described further below, to draw the waste material into the waste containers 102, 104 from the sites in proximity to the patient. With the vacuum present, waste material is drawn through the suction lines S, manifolds M, and finally through waste ports 128 defined in the caps 118, 124 to enter the canisters 114, 120. Users can select to simultaneously collect waste material in both canisters 114, 120 or one at a time.

A main controller 130 operates the waste collection unit 100. The main controller 130 may comprise a plurality of sub-controllers, each including one or more microprocessors, processors, systems on a chip, etc. to operate certain features of the waste collection unit 100. The sub-controllers may communicate with the main controller 130 along a communications bus or by other conventional methods. An on-board control panel CP is in communication with the main controller 130 to allow user selected operation of the waste collection unit 100.

The vacuum circuit 126 provides independently controllable vacuum levels in each of the waste containers 102, 104. As a result, the user can establish different vacuum levels for the waste containers 102, 104 depending on the particular needs of the medical procedure being performed. The vacuum circuit 126 comprises a vacuum source for providing the vacuum available to the waste containers 102, 104. In some embodiments, the vacuum source is a vacuum pump 132 supported on the cart 106 to provide an on-board vacuum pump. One such vacuum pump 132 is a Welch 2585 Series vacuum pump, available from Gardner Denver, Inc. of Niles, Illinois. The vacuum pump 132 may alternatively be a VT series rotary vane pump from Becker Pumps Corp. of Cuyahoga Falls, Ohio. The vacuum pump 132 communicates with vacuum ports VP of each of the waste containers 102, 104 to provide a vacuum in the waste containers 102, 104 to draw waste material into the waste containers 102, 104 through the suction lines S.

Upper and lower vacuum regulators 135, 136 are included in the vacuum circuit 126. The vacuum regulators 135, 136 are supported on the cart 106 for adjusting the vacuum levels in the waste containers 102, 104. The main controller 130 controls operation of the vacuum regulators 135, 136 through upper and lower vacuum controllers (e.g., separate microcontrollers) to maintain desired vacuum levels in each of the waste containers 102, 104. Knobs, dials, touch screen inputs, or the like, are in communication with the main controller 130, and disposed on the control panel CP, to allow the user to establish the desired vacuum levels in the waste containers 102, 104. Control of the vacuum levels in the waste containers 102, 104, as described in U.S. Pat. No. 7,621,898, entitled "Medical/Surgical Waste Collection Unit Including Waste Containers of Different Storage Volumes With Inter-container Transfer Valve and Independently Controlled Vacuum Levels," is hereby incorporated by reference herein. Alternatively, vacuum levels in the waste containers 102, 104 could be controlled by simply varying the speed of the vacuum pump 132, or by using separate, independently controlled vacuum pumps 132 for each of the waste containers 102, 104.

In one embodiment, the vacuum pump 132, is a positive displacement piston pump. The vacuum pump 132 has a drive shaft (not shown) and pistons (not shown) that operate to pull a vacuum and induce flow through a vacuum inlet 133, and to force air out of a vacuum outlet 134. The vacuum pump 132 may also be a rotary vane vacuum pump or any other type of vacuum pump suitable for drawing waste materials into the waste containers 102, 104.

Figure 4:
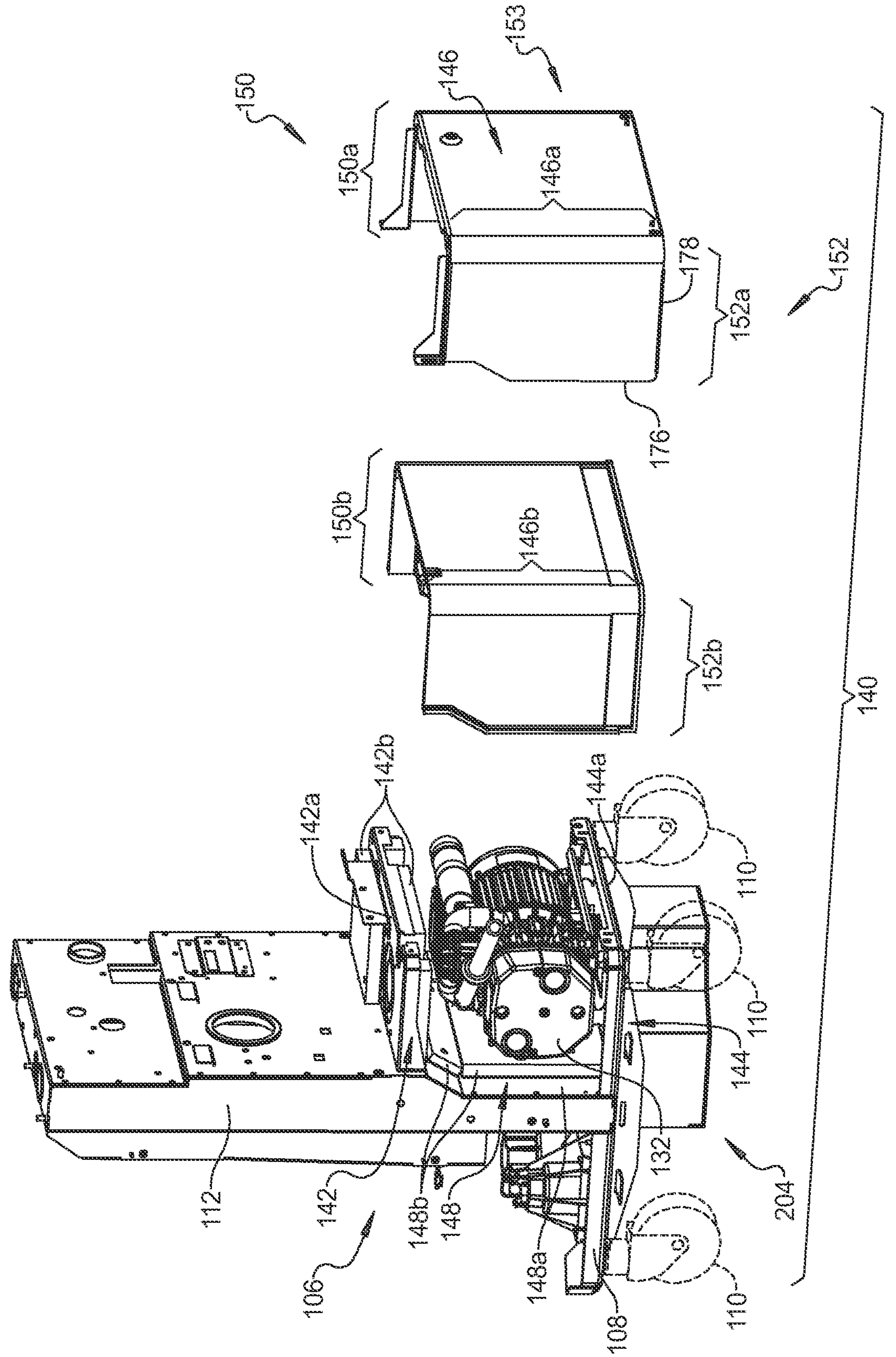
FIG. 4 is a partially exploded view illustrating parts of the waste collection unit including a vacuum source and a sound attenuating enclosure for the vacuum source.

Referring to FIGS. 3 and 4, a sound attenuating enclosure 140 including acoustic absorbing material and/or other structure substantially surrounds the vacuum pump 132 to attenuate noise associated with the vacuum pump 132. The sound attenuating enclosure 140 is designed to reduce noise that results from operation of the vacuum pump 132 on the waste collection unit 100, while at the same time receiving cooling air to manage heat generated by the vacuum pump 132. The sound attenuating enclosure 140 is designed to house the vacuum pump 132 in a manner that provides necessary cooling to keep the vacuum pump 132 running at acceptable temperatures and facilitates maximum noise attenuation within the allowed space envelope within the waste collection unit 100.

Sound waves associated with the vacuum pump 132 emanate from the waste collection unit 100 and into the environment external to the waste collection unit 100. There are several potential paths for these sound waves. For instance, there may be: (1) sound waves carried in fluid drawn through the vacuum pump 132; (2) sound waves carried in the cooling air passing around the vacuum pump 132, as described further below; (3) sound waves that are transmitted acoustically through materials forming the sound attenuating enclosure 140; and (4) sound waves generated by structure borne vibrations starting from the vacuum pump 132 and dispersing to the sound attenuating enclosure 140 through any solid contact points. The sound attenuating enclosure 140 operates to mitigate these sound waves before they reach the user outside of the sound attenuating enclosure 140.

In some versions, the sound attenuating enclosure 140 is able to attenuate these sound waves so that the noise, as measured outside of the sound attenuating enclosure 140, is significantly reduced, as compared to the noise made by the vacuum pump 132 without the sound attenuating enclosure 140.

Figure 5:
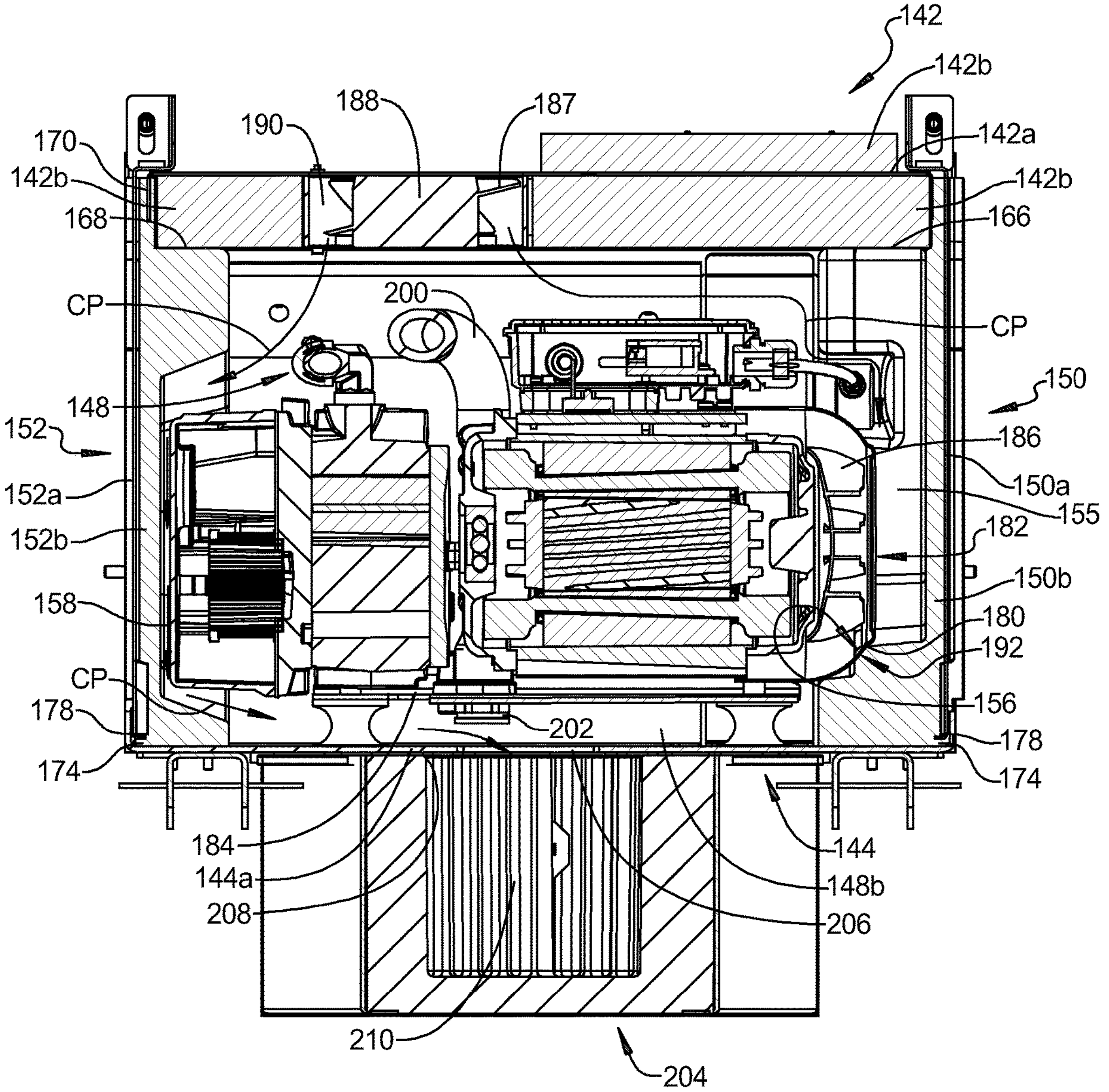
FIG. 5 is a cross-sectional view illustrating a chamber within the sound attenuating enclosure.
Figure 6:
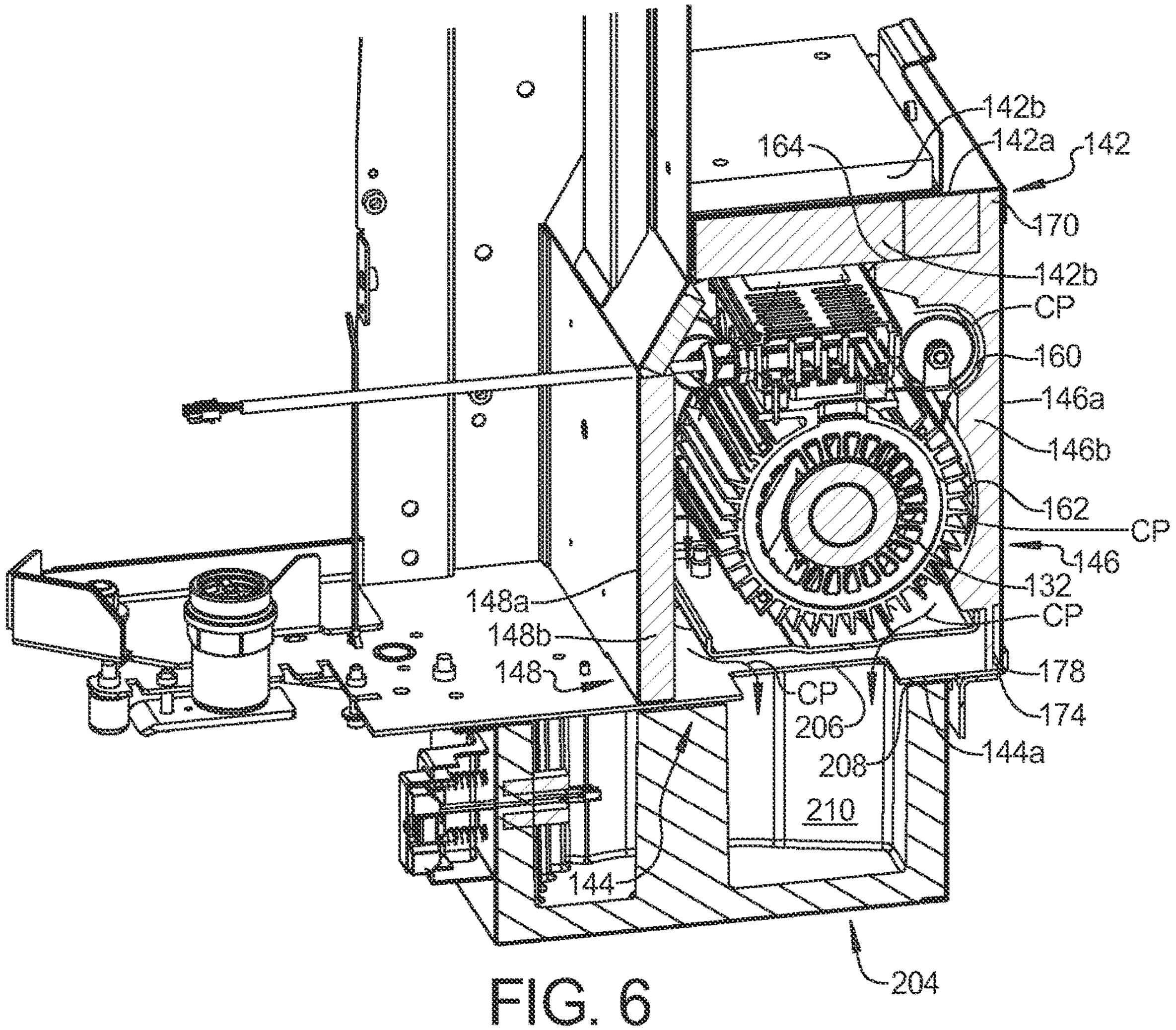
FIG. 6 is a cross-sectional view further illustrating the chamber within the sound attenuating enclosure.
Figure 6A:
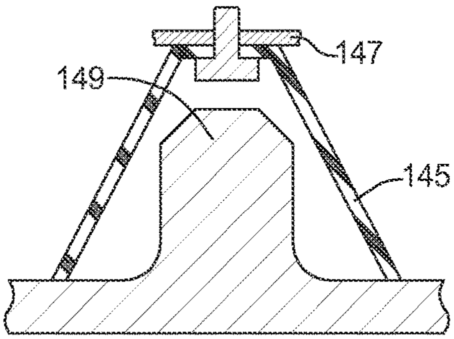
FIG. 6A is a cross-sectional view illustrating locators for the vacuum source.

Referring to FIGS. 4-6, the sound attenuating enclosure 140 comprises a top section 142, a bottom section 144, a front section 146, a rear section 148, and opposing right and left side sections 150, 152. Collectively, these sections 142, 144, 146, 148, 150, 152 define a sound attenuating chamber. The vacuum pump 132 may be mounted in the sound attenuating chamber by securing the vacuum pump 132 to the bottom section 144 via bolts. The bolts may be outfitted with resilient members (not shown) that absorb the vibration of the vacuum pump 132 during operation to minimize the vibration transferred to the bottom section 144 that could result in audible noise and a noticeable vibration in the waste collection unit 100 by the user. In other embodiments, the vacuum pump 132 may be disposed in the sound attenuating enclosure 140 without requiring any mechanical fastening to the bottom section 144 and may merely rest on the bottom section 144 via feet fixed to the vacuum pump 132. Further, the vacuum pump 132 may rest on the bottom section 144 with one or more resilient members (e.g., foam, rubber isolators, springs, etc.) placed between a base of the vacuum pump 132 and the bottom section 144. Referring to FIG. 6A, for example, the feet of the vacuum pump 132 comprise resilient members 145 (only one shown) having a conical shape that are bolted to a base frame 147 of the vacuum pump 132. Locators 149 (e.g., studs; only one shown) are disposed on the bottom section 144 and extend upwardly into an opening in the resilient members 145 so that the locators 149 generally locate the feet, but without requiring any rigid connection.

Each of the top section 142, the bottom section 144, the front section 146, the rear section 148, and the opposing right and left side sections 150, 152 comprise a noise barrier 142*a*, 144*a*, 146*a*, 148*a*, 150*a*, 152*a* that substantially surrounds the vacuum pump 132 on all sides and which reflects sound waves back into the sound attenuating chamber instead of letting all the sound waves pass into the environment. In one embodiment, the noise barriers 142*a*, 144*a*, 146*a*, 148*a*, 150*a*, 152*a* comprise aluminum walls. In other embodiments, the noise barriers 142*a*, 144*a*, 146*a*, 148*a*, 150*a*, 152*a* comprise steel walls. The noise barriers 142*a*, 144*a*, 146*a*, 148*a*, 150*a*, 152*a* could be formed of other similarly dense and rigid materials such as ceramic, concrete, and the like. The walls may be sheet metal walls having a thickness of ½" or less, ⅜" or less, and the like. The noise barriers 142*a*, 144*a*, 146*a*, 148*a*, 150*a*, 152*a* may comprise one or more separate walls fastened together and to the vertical chassis 112 as shown. In the embodiment shown, the noise barriers 146*a*, 150*a*, 152*a* associated with the front and side sections 146, 150, 152, comprise a single piece of sheet metal 153 formed into a U-shape.

In some of the sections 142, 144, 146, 148, 150, 152 of the sound attenuating enclosure 140, the space between the noise barriers 142*a*, 144*a*, 146*a*, 148*a*, 150*a*, 152*a* and the vacuum pump 132 is filled with a foam material that absorbs sound energy and transforms it into heat energy which is dissipated to the environment as heat instead of sound. In the embodiment shown, each of the top, front, rear, and side sections 142, 146, 148, 150, 152 comprise top, front, rear, and side foam portions 142*b*, 146*b*, 148*b*, 150*b*, 152*b* formed of the foam material, such that the sound attenuating enclosure 140 is at least partially formed of the foam material. The foam material is configured to attenuate noise generated by the vacuum pump 132 during operation. In particular, the foam material helps to attenuate noise through all of the sound wave paths previously described. For instance, the foam material: (1) absorbs the sound waves escaping from the fluid coming out of the vacuum pump 132; (2) absorbs the sound waves escaping the cooling air passing around the vacuum pump 132; (3) adds mass and damping to the sections 142, 144, 146, 148, 150, 152 to improve their transmission loss and reduce their efficiency at converting vibrations to sound waves.

The foam material used for each of the foam portions 142*b*, 146*b*, 148*b*, 150*b*, 152*b*, may be the same or different. In some embodiments, the foam material comprises an insulation material, such as a thermoset foam material, and more specifically, a thermoset polyurethane foam. The foam material may comprise a high density, thermoset polyurethane foam. The foam material may also comprise closed cell foam. In some embodiments, the foam material may comprise polyurethane foam with graphite or other additives. In further embodiments, the foam material may be substituted by other types of insulation, such as silica aerogels, microporous silicate insulation, and the like. Any combination of sound wave absorbing materials can be used to form the foam portions 142*b*, 146*b*, 148*b*, 150*b* (also referred to as sound absorbing portions). In some embodiments, the foam portions 142*b*, 146*b*, 148*b*, 150*b* have a nominal wall thickness of at least 0.15 inches, of at least 0.17 inches, or of at least 0.25 inches. In some locations, the foam portions 142*b*, 146*b*, 148*b*, 150*b* have thicknesses of greater than 0.5 inches. Thus, the foam portions 142*b*, 146*b*, 148*b*, 150*b* may have varying thicknesses to further improve noise attenuation where possible.

In order to maximize the foam volume and therefore maximize noise attenuation, the foam portions 142*b*, 146*b*, 148*b*, 150*b*, 152*b* may be molded, die cut, sculpted, etc., into desired shapes. Accordingly, the foam portions 142*b*, 146*b*, 148*b*, 150*b*, 152*b* can be shaped to mimic the geometry of the vacuum pump 132. In other words, owing to the formed shapes of the foam portions 142*b*, 146*b*, 148*b*, 150*b*, 152*b*, the sections 142, 146, 148, 150, 152 may have an interior shaped to generally conform to a shape of the vacuum pump 132, as shown in FIGS. 5 and 6. In some cases, an inner surface of one or more of the foam portions 142*b*, 146*b*, 148*b*, 150*b*, 152*b* may be contoured so that the inner surface matches an outer profile of the vacuum pump 132 or so that a gap of equal dimension is formed between the inner surface and the outer profile, as shown in FIG. 6.

Outer surfaces of the foam portions 142*b*, 146*b*, 148*b*, 150*b*, 152*b* may also be formed to conform to a shape of the noise barriers 142*a*, 146*a*, 148*a*, 150*a*, 152*a*, against which the foam portions 142*b*, 146*b*, 148*b*, 150*b*, 152*b* abut. In the embodiment shown, most of the noise barriers 142*a*, 146*a*, 148*a*, 150*a*, 152*a* have a planar inner surface. As a result, the foam portions 142*b*, 146*b*, 148*b*, 150*b*, 152*b* can be molded or otherwise formed to have an abutting planar outer surface. Adhesive may additionally be used to fix the outer surfaces of the foam portions 142*b*, 146*b*, 148*b*, 150*a*, 152*a* to the noise barriers 142*a*, 146*a*, 148*a*, 150*a*, 152*a*.

The foam portions 142*b*, 146*b*, 148*b*, 150*b*, 152*b* can be made of separate foam pieces or can be integrally formed as one piece. Any combination of these foam portions 142*b*, 146*b*, 148*b*, 150*b*, 152*b* can be integrally formed as one piece or formed separately. Referring to FIGS. 7-11, the foam portions 146*b*, 150*b*, 152*b* are integrally formed as a U-shaped foam piece 154. The foam piece 154 is generally congruent with the single piece of sheet metal 153 (see FIG. 4). Collectively, the foam piece 154 and the piece of sheet metal 153 form the front section 146 and the side sections 150, 152 of the sound attenuating enclosure 140.

Figure 7:
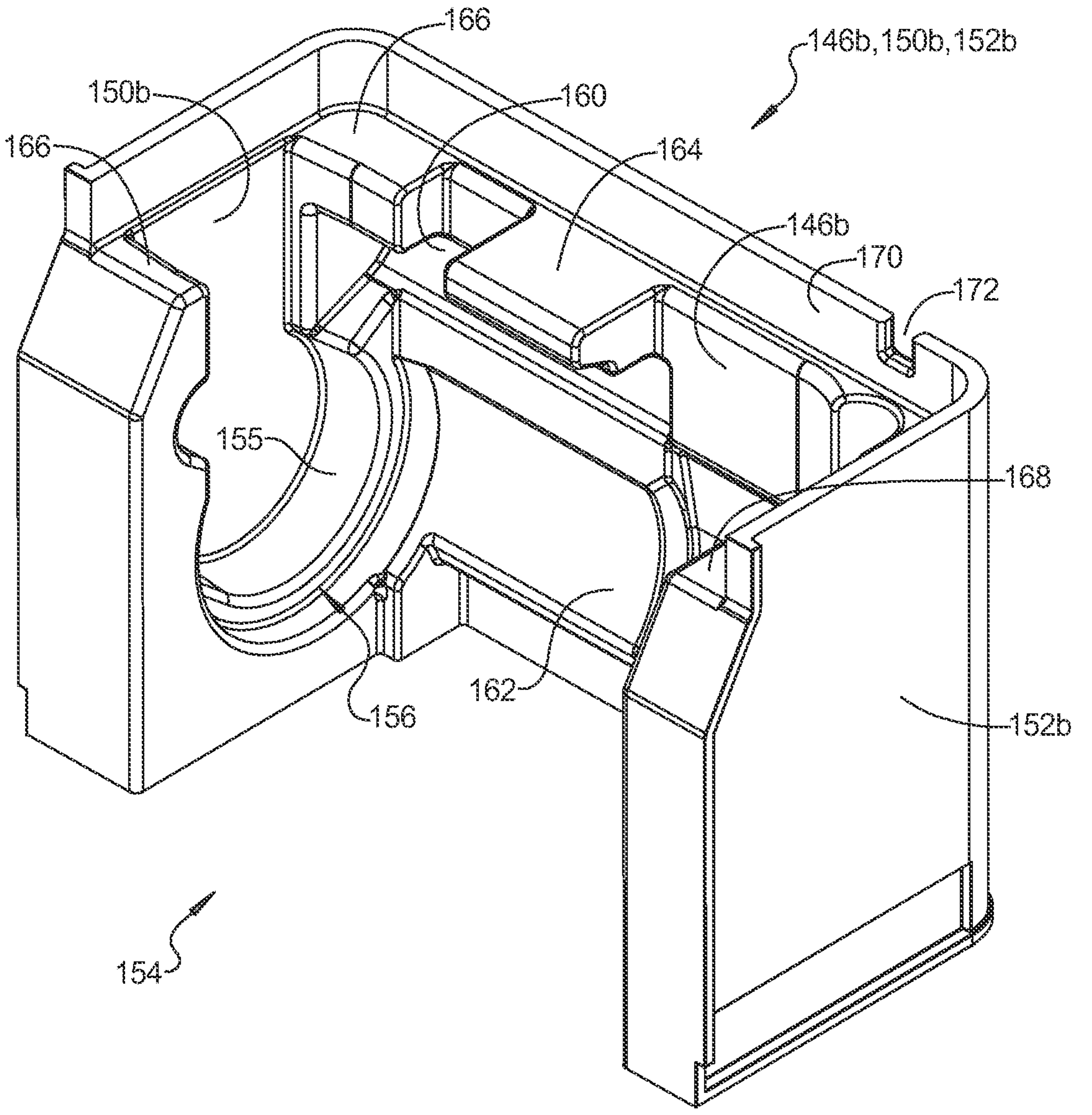
FIG. 7 is a rear perspective view of a foam piece forming part of the sound attenuating enclosure.
Figure 8:
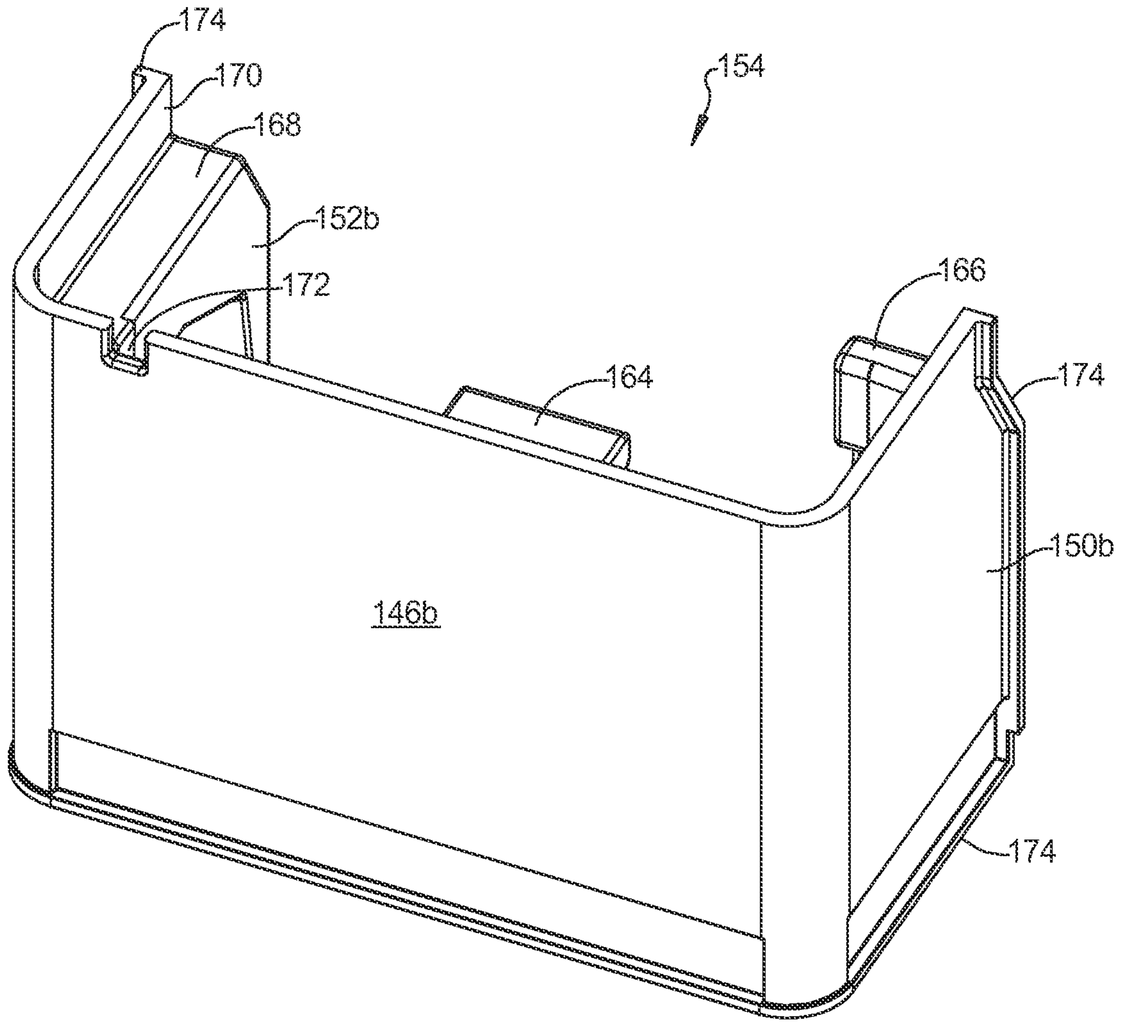
FIG. 8 is a front perspective view of the foam piece of FIG. 7.
Figure 10:
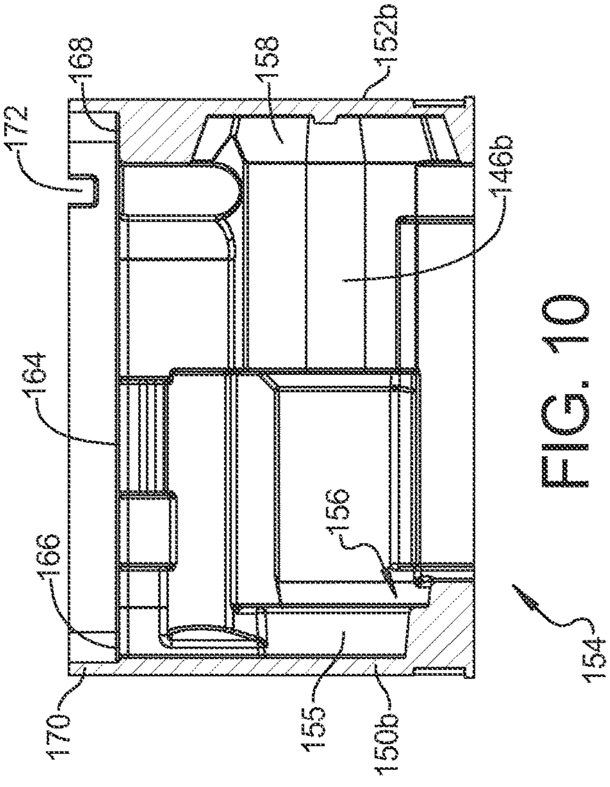
FIG. 10 is a cross-sectional view of the foam piece of FIG. 7 taken generally along the line 10-10 in FIG. 9.
Figure 9:
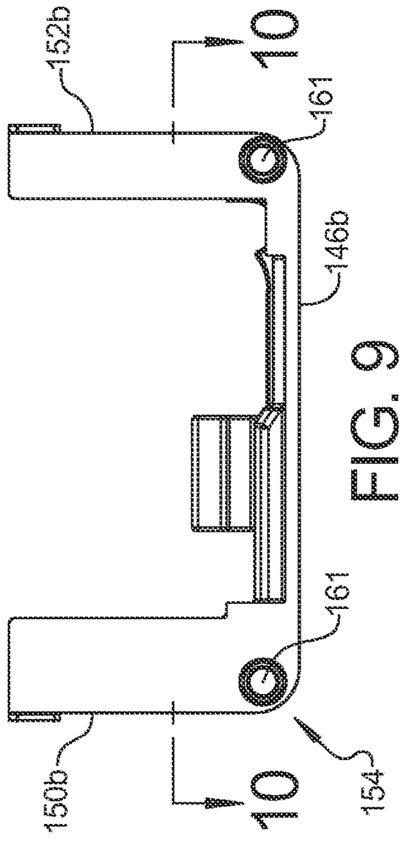
FIG. 9 is a bottom view of the foam piece of FIG. 7.
Figure 11:
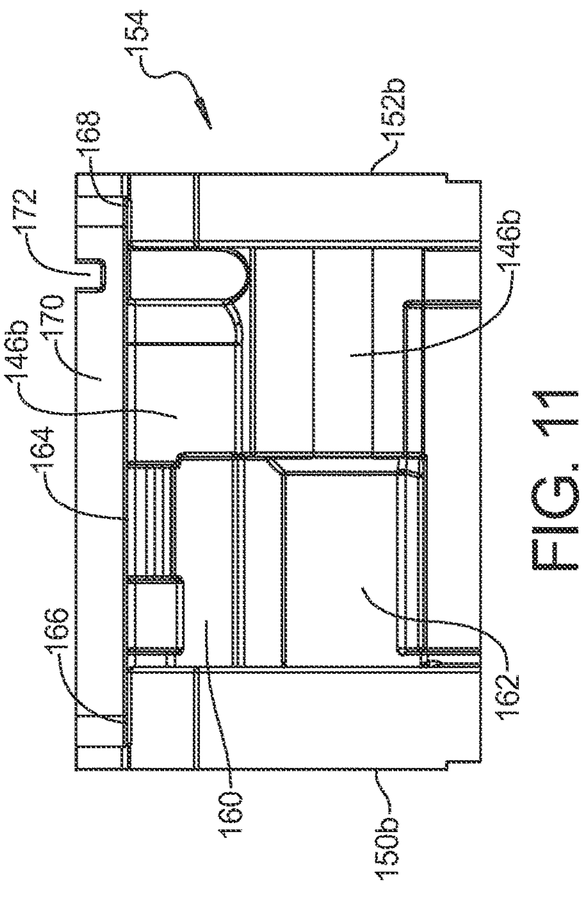
FIG. 11 is a rear view of the foam piece of FIG. 7.

Geometric features can be molded or otherwise formed on the inner surfaces of the foam piece 154 to accommodate the vacuum pump 132, flow paths, cables, hoses, electrical wires, bolts, or other components of the waste collection unit 100. For instance, as shown in FIGS. 5 and 7, the right side foam portion 150*b* defines a partially cylindrical pocket 155 for receiving a first end of the vacuum pump 132. The right side foam portion 150*b* also has an integrally formed seat 156 against which the first end of the vacuum pump 132 abuts. As shown in FIGS. 5 and 10, the left side foam portion 152*b* defines a second generally cylindrical pocket 158 for receiving a second end of the vacuum pump 132. The front foam portion 146*b* has a pair of arcuate recesses 160, 162 to accommodate other features of the vacuum pump 132 (see FIG. 6). With reference to FIG. 9, inner cylindrical counterbores 161 may be provided to accommodate protruding bolts or the like in the bottom section 144.

The foam portions 142*b*, 146*b*, 148*b*, 150*b*, 152*b* may be configured so that, when assembled with the noise barriers 142*a*, 146*a*, 148*a*, 150*a*, 152*a*, each of the foam portions 142*b*, 146*b*, 148*b*, 150*b*, 152*b* abut an adjacent foam portion to further attenuate noise inside the sound attenuating enclosure 140. For instance, front and side foam portions 146*b*, 150*b*, 152*b* abut by virtue of being integrally formed as one piece. Further, each of the front and side foam portions 146*b*, 150*b*, 152*b* abuts the top foam portions 142*b*. More specifically, referring to FIGS. 5 and 6, each of the front and side foam portions 146*b*, 150*b*, 152*b* has a shelf 164, 166, 168 upon which to receive and abut against the top foam portions 142*b*.

The foam piece 154 has a lip 170 extending upwardly from each shelf 164, 166, 168 to laterally surround one or more of the top foam portions 142*b*. The lip 170 may be integrally formed as part of the single foam piece 154 to further seal against the escape of unwanted noise when the foam piece 154 is assembled adjacent to the top foam portions 142*b*. Cutouts 172 may be formed in the lip 170 to accommodate wires, hoses, and the like.

One or more of the foam portions 142*b*, 146*b*, 148*b*, 150*b*, 152*b* may further comprise a flange 174 (see FIG. 8) formed of the foam material to seal between metal portions of the sound attenuating enclosure 140, such as between connected portions of the noise barriers 142*a*, 144*a*, 146*a*, 148*a*, 150*a*, 152*a*. In the embodiment shown, the flange 174 is integrally formed in the foam piece 154. The flange 174 is arranged to abut against rear and bottom edges 176, 178 of the side noise barriers 150*a*, 152*a* such that the flange 174 is captured and compressed between the rear edges 176 and the chassis 112 and between the bottom edge 178 and the bottom noise barrier 144*a* when the single piece of sheet metal 153 is mounted to the chassis 112 and the bottom noise barrier 144*a*, as shown.

The flange 174 (also referred to as a gasket) minimizes any openings through which sound waves can freely travel. Such openings can otherwise provide a 'flanking path' where sound escapes the sound attenuating enclosure 140 because of a leak. Compressing the gasket forms a mostly-rigid seal, or barrier, that the sound cannot penetrate easily. If the gasket is not compressed, but just disposed in a relaxed state, the gasket would absorb some sound energy, but much would pass right through. Compression of the gasket makes the gasket denser to resist the passage of sound waves. The gasket also functions to limit vibrations between the metal portions.

In some embodiments (not shown), one or more of the noise barriers 142*a*, 146*a*, 148*a*, 150*a*, 152*a* may be embedded into the foam material of the foam portions 142*b*, 146*b*, 148*b*, 150*b*, 152*b*. In this case, the foam material may be molded around the noise barriers 142*a*, 146*a*, 148*a*, 150*a*, 152*a*. Further, the noise barriers 142*a*, 146*a*, 148*a*, 150*a*, 152*a* may comprise at least one of metal and plastic and may be flexible or rigid.

Since vibrations can be transmitted through the foam portions 142*b*, 146*b*, 148*b*, 150*b*, 152*b*, the sound attenuating enclosure 140 is formed so that, in many locations, there is generally a gap between the foam portion 142*b*, 146*b*, 148*b*, 150*b*, 152*b* and an outer surface of the vacuum pump 132. This allows for enough room so that when the vacuum pump 132 vibrates, such as with a displacement of approximately ⅛", the vacuum pump 132 does not contact the foam material and no vibrations are transmitted. In some cases, the gaps created between the foam material and the outer surface of the vacuum pump 132 are for purposes of allowing cooling air flow as described further below.

Referring to FIGS. 5 and 6, to ensure that the vacuum pump 132 does not overheat while operating in the sound attenuating enclosure 140, cooling air paths CP are incorporated into the sound attenuating enclosure 140 so that room temperature air is pulled across the vacuum pump 132 and is then directed out of the sound attenuating enclosure 140 to carry away heat from the sound attenuating chamber. Gaps may be formed between the vacuum pump 132 and the foam portions 142*b*, 146*b*, 148*b*, 150*b*, 152*b* to provide the cooling air paths CP. For instance, in the embodiment shown, the pocket 158 and the arcuate recesses 160, 162 are sized so that a gap is formed between the vacuum pump 132 and the foam portions 152*b*, 146*b* to provide cooling air paths CP.

One or more fans integrated in the vacuum pump 132 and/or a separate fan may be employed to provide the cooling air for the cooling air paths CP. In the embodiment shown, the vacuum pump 132 comprises a casing 180 defining a casing inlet 182 and at least one casing outlet 184. The vacuum pump 132 further comprises an integrated cooling fan 186 (driven by the same motor as the pump components) for drawing the cooling air into the casing 180 at the casing inlet 182 and exhausting warmed cooling air from the casing outlet 184. In addition, another cooling air fan 187 and motor 188 is mounted to the upper noise barrier 148*a*. In particular, the cooling air fan 187 and motor 188 are mounted in an enclosure inlet 190 of the sound attenuating enclosure 140. The enclosure inlet 190 is defined through the top section 142.

In some embodiments, the cooling fan 186 of the vacuum pump 132 automatically operates any time the main controller 130 operates the vacuum pump 132, especially in cases where the cooling fan 186 is driven by the same motor as the vacuum pump 132. In other embodiments, the cooling fan 186 may have a dedicated motor and be capable of being independently operated whenever the waste collection unit 100 is active, regardless of whether the vacuum pump 132 is actively drawing vacuum in either of the waste containers 102, 104. Similarly, the cooling air fan 187 and motor 188 may be controlled by the main controller 130 to only operate while the vacuum pump 132 is operating or whenever the waste collection unit 100 is active. The cooling air fan 187 and motor 188 may be capable of variable speed operation in order to increase or decrease the flow of cooling air into the sound attenuating enclosure 140.

The cooling air fan 187 may be located at any suitable location to provide cooling air inside the sound attenuating enclosure 140. The cooling air fan 187 may be located either inside or outside of the sound attenuating enclosure 140. The cooling air fan 187 may be located at the enclosure inlet 190 to push cooling air into the sound attenuating enclosure 140 or may be located at an enclosure outlet 206 to pull the cooling air into the sound attenuating enclosure 140. In the embodiment shown, a separate inlet enclosure (also referred to as an inlet plenum) may partially surround the enclosure inlet 190 to provide additional attenuation of the sound waves that escape from the sound attenuating enclosure 140 through the enclosure inlet 190.

The cooling air paths CP were designed to accommodate at least a portion of the cross sectional flow area at the casing inlet 182 to the vacuum pump 132. In some embodiments, the cooling air paths CP have the same or greater cross sectional area as the casing inlet 182. The cooling air is drawn down through the enclosure inlet 190, which is dimensioned to be at least as large in area as the cooling air paths CP in one embodiment to ensure no restriction at the enclosure inlet 190, but could be smaller in some cases owing to various design constraints. Some of the cooling air paths CP then guide the cooling air into the casing inlet 182 where the cooling fan 186 is located. The cooling air then flows throughout a base of the vacuum pump 132, then up along an outside of pump cylinders, or other pump structures performing similar functions, and leaves the vacuum pump 132 through one or more of the casing outlets 184.

In some cases, if the vacuum pump 132 is not provided with one or more cooling fans 186, 187 and/or cooling air paths CP to dissipate the generated heat energy, the vacuum pump 132 may overheat and trip a thermal protection switch. In order to avoid this, ambient air is provided by the enclosure inlet 190 to flow through the casing 180 of the vacuum pump 132 to pick up excess heat, and then carry the heat away from the vacuum pump 132 and into the atmosphere. By providing indirect cooling air paths CP for the incoming and outgoing cooling air and lining the cooling air paths CP with the noise absorbing material, considerable noise attenuation is achieved.

A cooling air barrier 192 is provided to prevent the cooling air from recirculating back into the casing 180 of the vacuum pump 132 once it has absorbed heat from the vacuum pump 132. More specifically, the cooling air paths CP are configured so that the cooling air that exits the casing outlet 184 is limited from returning back to the casing inlet 182. This is accomplished in part by the integrally formed seat 156 against which the first end of the vacuum pump 132 abuts. As shown in FIGS. 5 and 7, the integrally formed seat 156 extends around an entire bottom half of the first end of the vacuum pump 132 so that air flow is prevented from entering into the partially cylindrical pocket 155 from below. As a result, cooling air that exits the casing 180 at the casing outlet 184 (see FIG. 5) is unable to pass between the bottom of the vacuum pump 132 and the right side foam portion 150*b*. This prevents the now warmed cooling air from being re-circulated back into the casing inlet 182. However, the pocket 155 is open from the top so that cooling air from the enclosure inlet 190 is able to easily follow one of the cooling paths CP to the casing inlet 182. Thus, this interface between the vacuum pump 132 and the right side foam portion 150*b* acts as a barrier between incoming ambient cooling air and the air heated by the vacuum pump 132. Thus, the sound attenuating enclosure 140 engages the vacuum pump 132 at a first location, but is still spaced from the vacuum pump 132 at least at a second location to define the cooling air paths CP for the cooling air.

Figure 12:
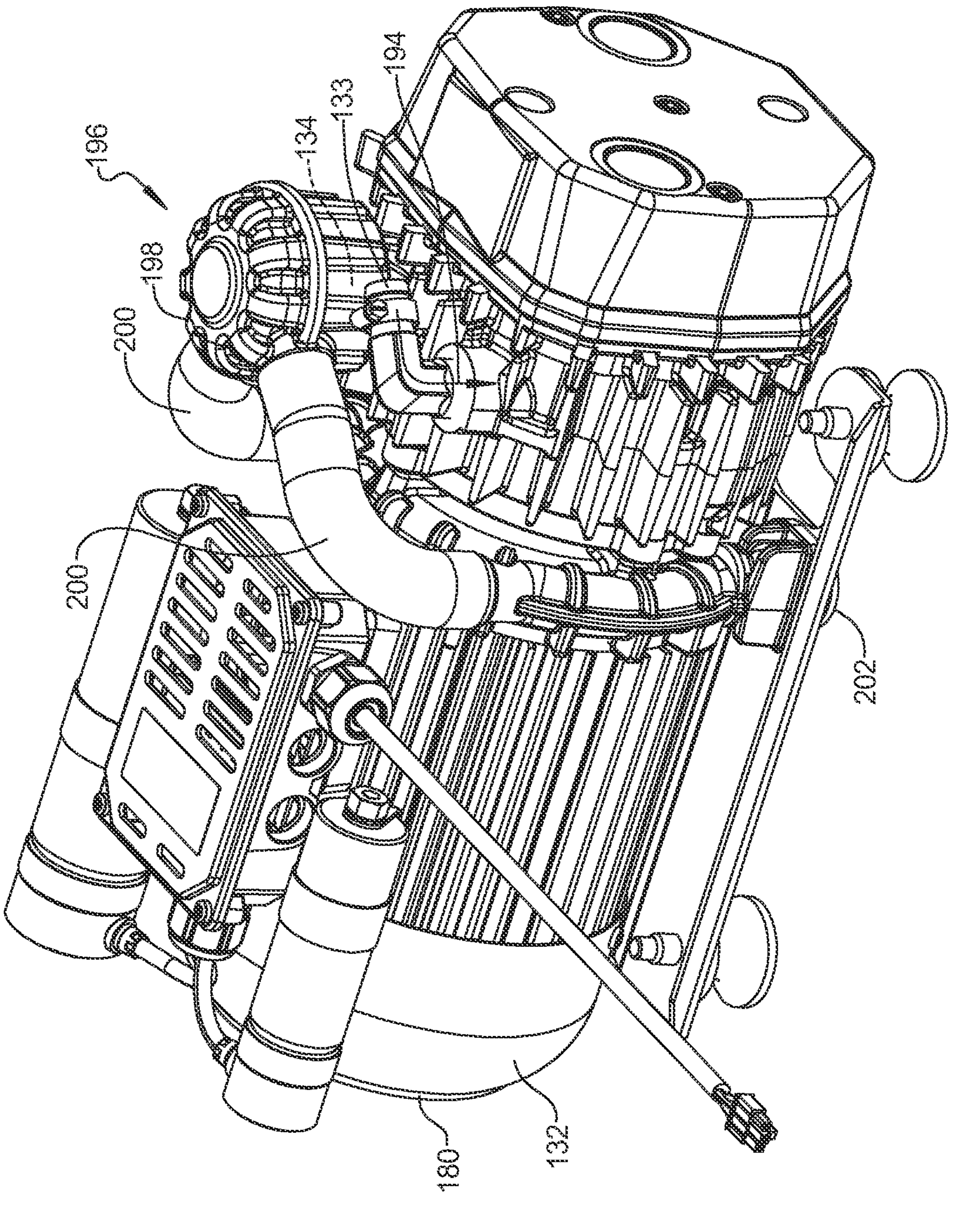
FIG. 12 is a perspective view of the vacuum source.
Figure 13:
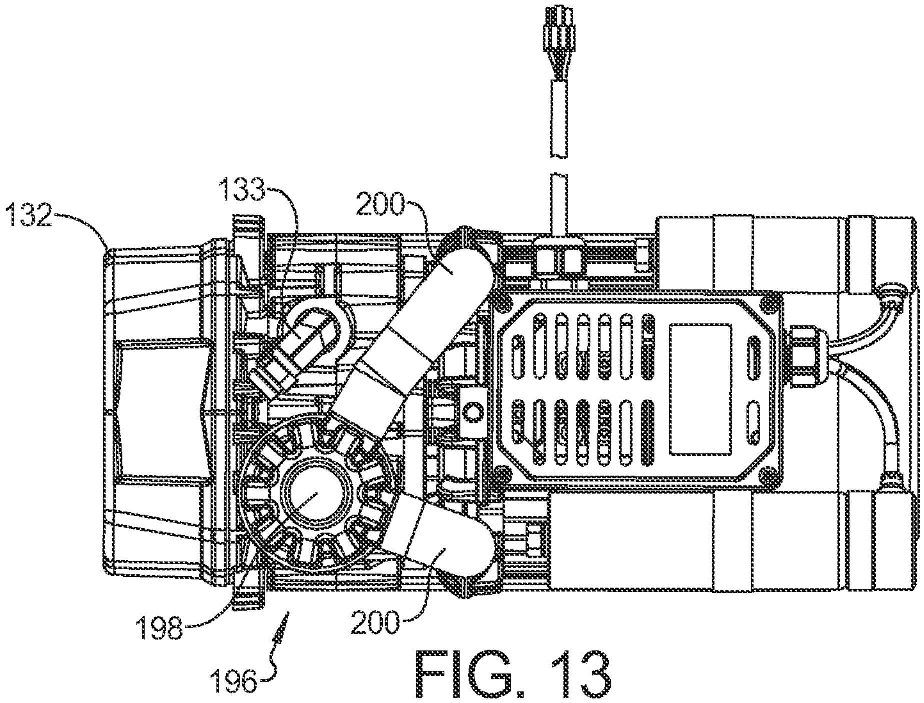
FIG. 13 is a top view of the vacuum source.
Figure 14:
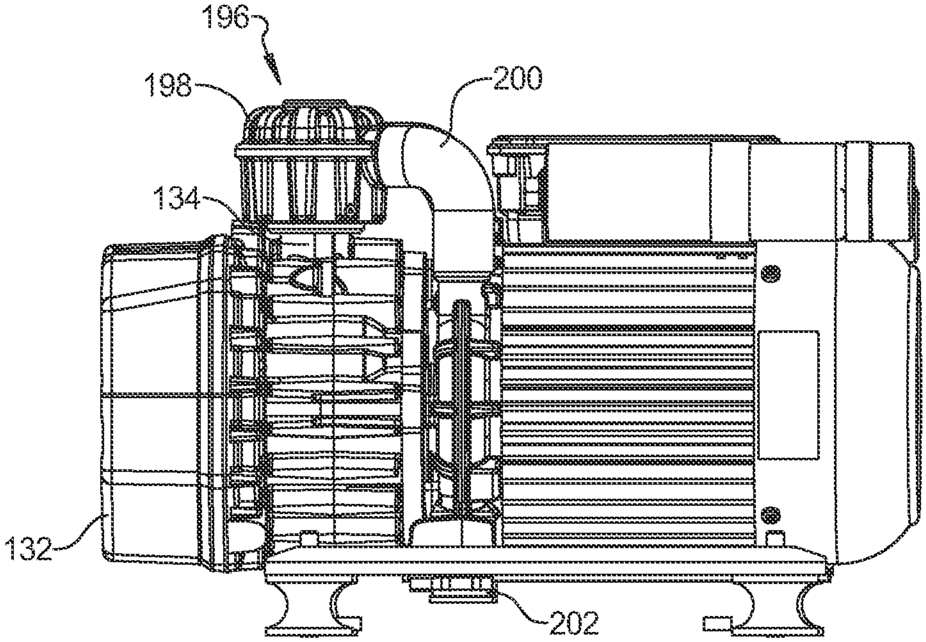
FIG. 14 is a side view of the vacuum source.

Referring to FIGS. 12-14, the vacuum pump 132 defines a vacuum passage 194 to carry air through the vacuum pump 132. The vacuum passage 194 extends from the vacuum inlet 133, to receive the air, and the vacuum outlet 134, to direct pressurized air from the vacuum pump 132. In the version shown in FIGS. 12-14, the pressurized air leaves the vacuum passage 194 and enters an exhaust assembly 196 comprising a muffler 198 and two exhaust hoses 200 extending from the muffler 198. The exhaust hoses 200 define separate exhaust passages through which pressurized air is exhausted. The pressurized air may carry significant amounts of noise, but the muffler 198 is intended to attenuate some of the noise in combination with the sound attenuating enclosure 140. A check valve 202 is located in the exhaust passages to prevent backflow and to also serve as a noise attenuation mechanism. Other types of noise attenuation mechanisms could be used such as a muffler (e.g., absorption muffler, chambered muffler, etc.), expansion chamber, Helmholtz resonator, quarter wave resonator/tube, low-pass filter, band-stop filter, and the like.

Once the cooling air has traveled through the casing 180 of the vacuum pump 132 and drawn heat from the vacuum pump 132, the warmed cooling air leaves the sound attenuating chamber and enters a plenum 204 (see FIG. 6). More specifically, the warmed cooling air passes through the enclosure outlet 206 defined in the bottom section 144 of the sound attenuating enclosure 140 and enters a plenum inlet 208 defined in the plenum 204. In other embodiments a separate conduit (e.g., tube) may be used to connect the sound attenuating enclosure 140 to the plenum 204. The enclosure outlet 206 and the plenum inlet 208 are aligned to facilitate the flow of the warmed cooling air. The plenum inlet 208 directs the warmed cooling air into a plenum chamber 210. By virtue of the volume of the plenum chamber 210, the warmed cooling air expands in the plenum 204 thereby further reducing the sound energy. The warmed cooling air then flows out of the plenum 204 and into the environment where it dissipates the heat drawn from the vacuum pump 132. Likewise, the pressurized air exhausted from the exhaust hoses 200 is also directed toward the plenum inlet 208 and enters the plenum chamber 210 along with the warmed cooling air (see FIG. 5). In some embodiments, the plenum 204 is considered to be part of the sound attenuating enclosure 140.

Referring to FIGS. 15-21, the plenum 204 comprises an outer noise barrier 212 mounted to the bottom section 144 of the sound attenuating enclosure 140. The noise barrier 212 may be of similar material as the noise barriers 142*a*, 144*a*, 146*a*, 148*a*, 150*a*, 152*a* previously described. The plenum 204 further comprises a plenum foam piece 214 (also referred to as a plenum sound absorbing piece) disposed between the noise barrier 212 and the plenum chamber 210 such that the noise barrier 212 covers the plenum foam piece 214, or the differently, walls of the noise barrier 212 are lined with foam material. The plenum foam piece 214 may be comprised of one or more of the materials previously described or a different material. Like the foam piece 154, the plenum foam piece may comprise one or more flanges 213 for sealing between an upper edge 215 of the noise barrier 212 and the bottom section 144 to provide similar functions as the flange 174.

The plenum chamber 210 is defined in the plenum foam piece 214. The plenum chamber 210 has a tortuous path between the plenum inlet 208 and a plenum outlet 216. By providing a tortuous path for the warmed cooling air and the exhausted air, both of which may carry varying levels of noise, the sound energy is further dissipated by virtue of the additional travel required between the plenum inlet 208 and the plenum outlet 216. Additionally, the plenum 204 comprises a plurality of sound absorbing projections 218. The sound absorbing projections 218 may be integrally formed with the foam piece 214, as shown, or could be separate. The sound absorbing projections 218 may comprise one or more of acoustic cones, acoustic pyramids, or acoustic triangular ridges. The sound absorbing projections 218 further attenuate sound from the warmed cooling air and the pressurized air from the vacuum pump 132.

The plenum outlet 216 is located on the rear of the plenum 204 as opposed to the bottom so that the heat is able to rise up and away. The plenum outlet 216 may be directed differently in other embodiments. Additionally, the plenum outlet 216 is separated from the enclosure inlet 190 to avoid the heated air from easily recirculating back into the sound attenuating enclosure 140. More specifically, the plenum outlet 216 exhausts the heated air beneath the waste collection unit 100 and the enclosure inlet 190 is defined in the top section 142, spaced sufficiently far from the plenum outlet 216, so that the heated air is not easily routed back into the sound attenuating enclosure 140.

Figure 22:
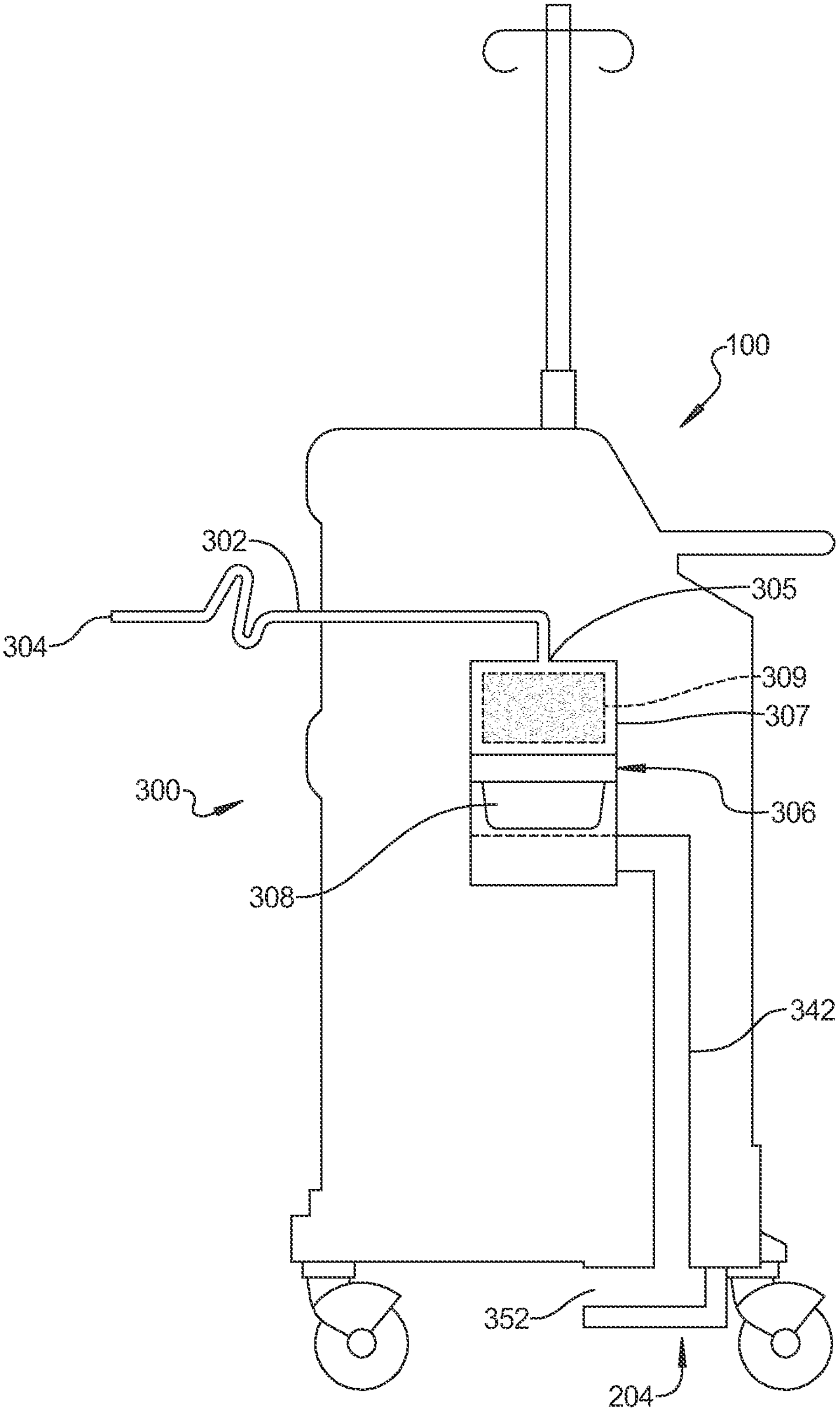
FIG. 22 is a schematic illustration of a smoke evacuation system of the waste collection unit.

Referring to FIG. 22, the waste collection unit 100 comprises a smoke evacuation system 300. The smoke evacuation system 300 is typically utilized for removing smoke from a fluid, such as air, during a medical procedure. However, other uses for the smoke evacuation system 300 are evident to those skilled in the art. The smoke evacuation system 300 could be integrally formed as part of the waste collection unit 100 as described herein, and could thus be mobile, permanently installed, or configured to be stationary. Additionally, or alternatively, the smoke evacuation system 300 could form a portable unit that is separate from or separable from the waste collection unit 100 as a stand-alone module.

The smoke evacuation system 300 includes a smoke conduit 302. The smoke conduit 302 includes an inlet 304, where the fluid is drawn into the conduit 302, and an outlet 305, where fluid is exhausted from the conduit 302 into a filter housing 307. A smoke evacuator, such as a blower assembly 306, is in fluid communication with the smoke conduit 302. The blower assembly 306 draws the fluid into the inlet 304 when the blower assembly 306 operates. The blower assembly 306 comprises a fan and a blower motor 308 for operating the fan. The blower assembly 306 may comprise a centrifugal fan and the blower motor 308 may be a brush motor. However, those skilled in the art realize alternative embodiments utilizing different implementations of the blower assembly 306. A smoke evacuation controller (not shown) may be used to control operation of the blower motor 308.

The smoke evacuation system 300 also includes a filter 309 in fluid communication with the smoke conduit 302. The filter 309 filters smoke from the smoke conduit 302, such that filtered air is exhausted from the filter housing 307. The filter 309 may be implemented as a plurality of filters and/or a plurality of filter elements. In one embodiment, the filter 309 comprises one filter element that includes activated carbon and another filter element that comprises a ULPA media. The filter 309 is replaceable such that users may change the filter 309 periodically. The filter 309 is preferably supported by the filter housing 307, which is supported on the portable cart 106.

Figure 23:
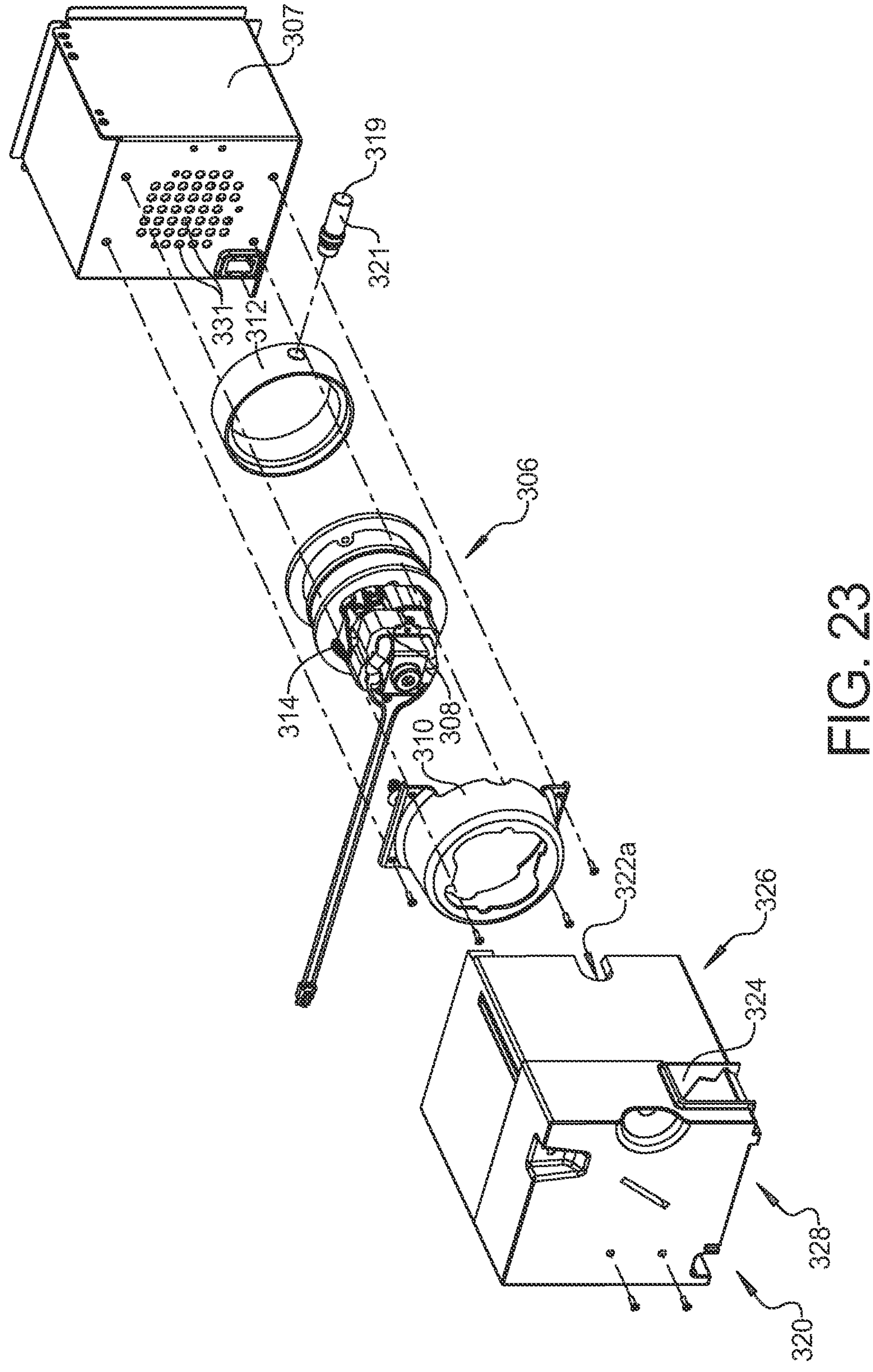
FIG. 23 is an exploded view of a smoke evacuator and sound attenuating enclosure for the smoke evacuator.
Figure 24:
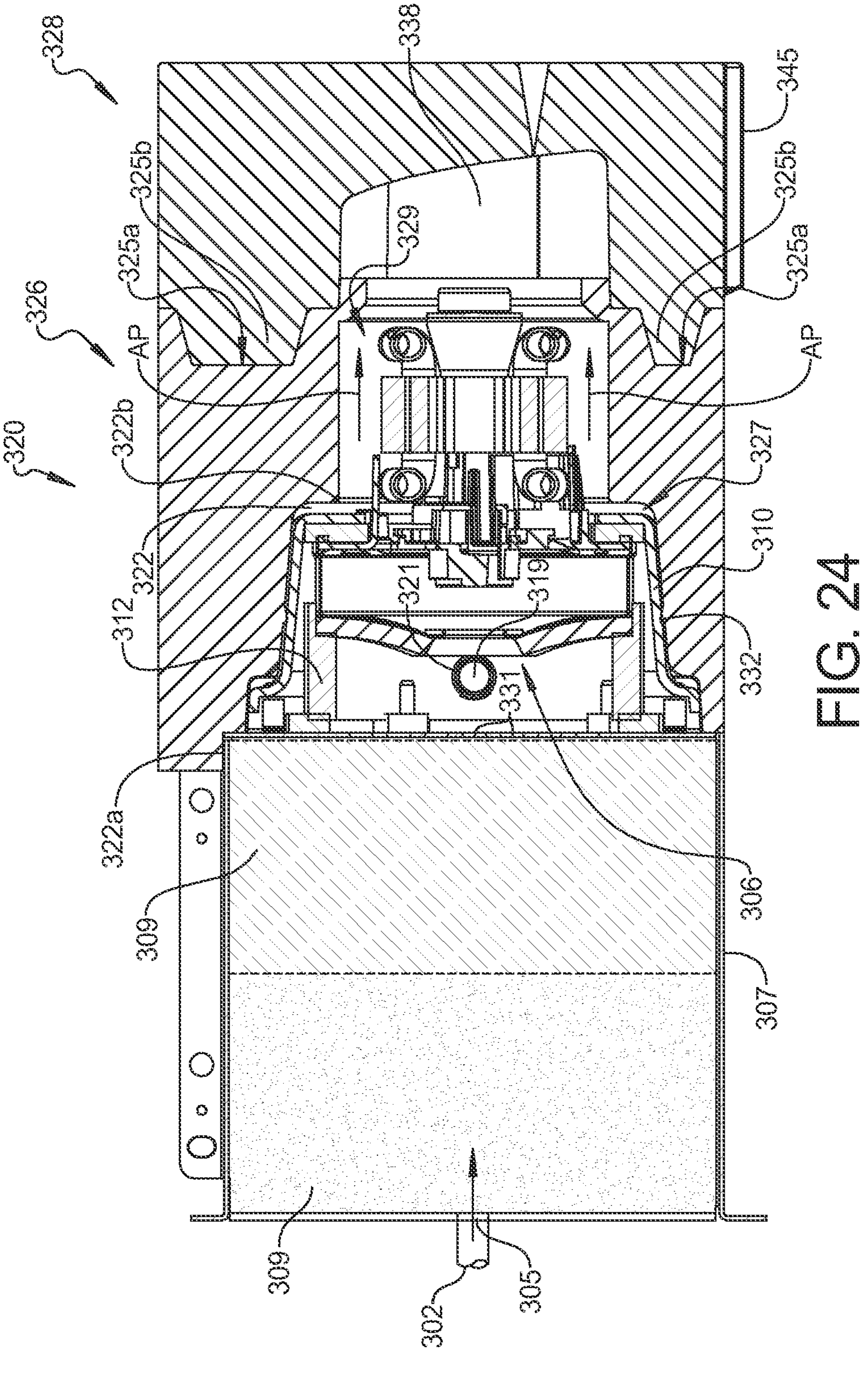
FIG. 24 is a cross-sectional view of the smoke evacuator and the sound attenuating enclosure for the smoke evacuator.

Referring to FIGS. 23 and 24, the blower assembly 306 is part of a module including the filter housing 307. In particular, a motor mount 310 and centering ring 312 are arranged to mount the blower assembly 306 to the filter housing 307 using fasteners. The blower assembly 306, when operated, draws the smoke from the smoke conduit 302 through outlet 305 into the filter housing 307 and through the filter(s) 309. The filtered air then passes through vent openings 331. The filtered air continues through exhaust openings 314 in the blower assembly 306. The filtered air may carry noise associated with operation of the blower assembly 306.

Another sound attenuating enclosure 320, in which the blower assembly 306 is disposed is used to attenuate the noise associated with operation of the blower assembly 306. The sound attenuating enclosure 320 defines an inlet chamber 322 extending between a first enclosure inlet **322*a* at one end of the sound attenuating enclosure 320 and a second enclosure inlet 322*b*. The second enclosure inlet 322*b* receives the filtered air that passes through the exhaust openings 314. The sound attenuating enclosure 320 further defines an enclosure outlet 324 for directing the filtered and warmed air from the blower assembly 306** to the environment.

In addition to the sound attenuating enclosure 320, a muffler 321 may be attached to the centering ring 312 to further attenuate noise associated with the blower assembly 306. During operation of the blower assembly 306, cooling air is drawn through the muffler 321 from inside the waste collection unit 100. More specifically, the muffler 321 defines an inlet 319 for the cooling air to enter the sound attenuating enclosure 320. This cooling air keeps the blower motor 308 cool enough to avoid failure, even if the smoke conduit 302 is occluded. By providing the muffler 321 at the inlet for this cooling air, noise from intake of the cooling air is at least partially attenuated. The muffler 321 also provides a tortuous path for noise that escapes from the blower assembly 306, which also helps to reduce the noise.

Figure 27:
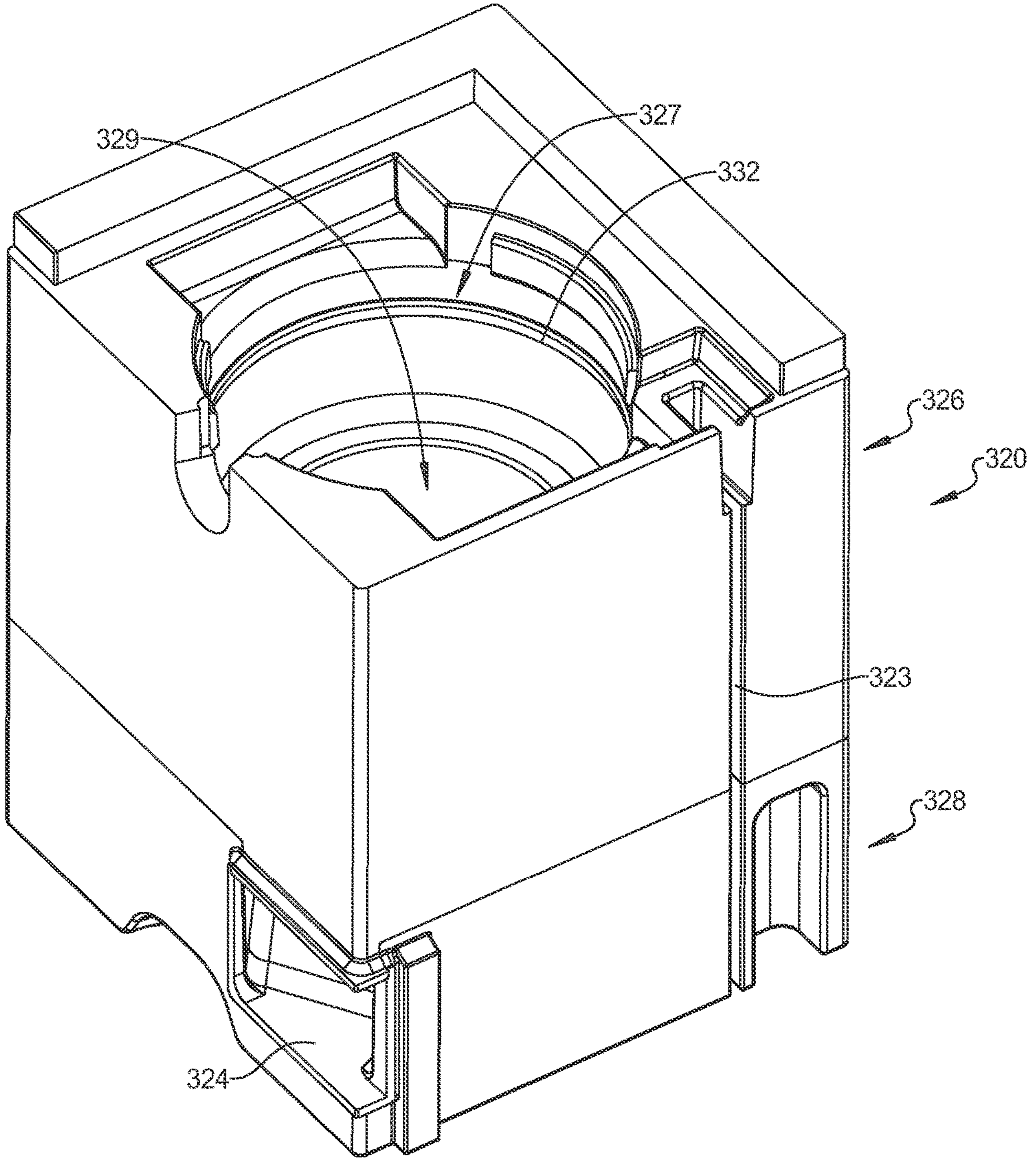
FIG. 27 is a perspective view of the two foam pieces of the sound attenuating enclosure for the smoke evacuator illustrating a channel for a wire harness.
Figure 28:
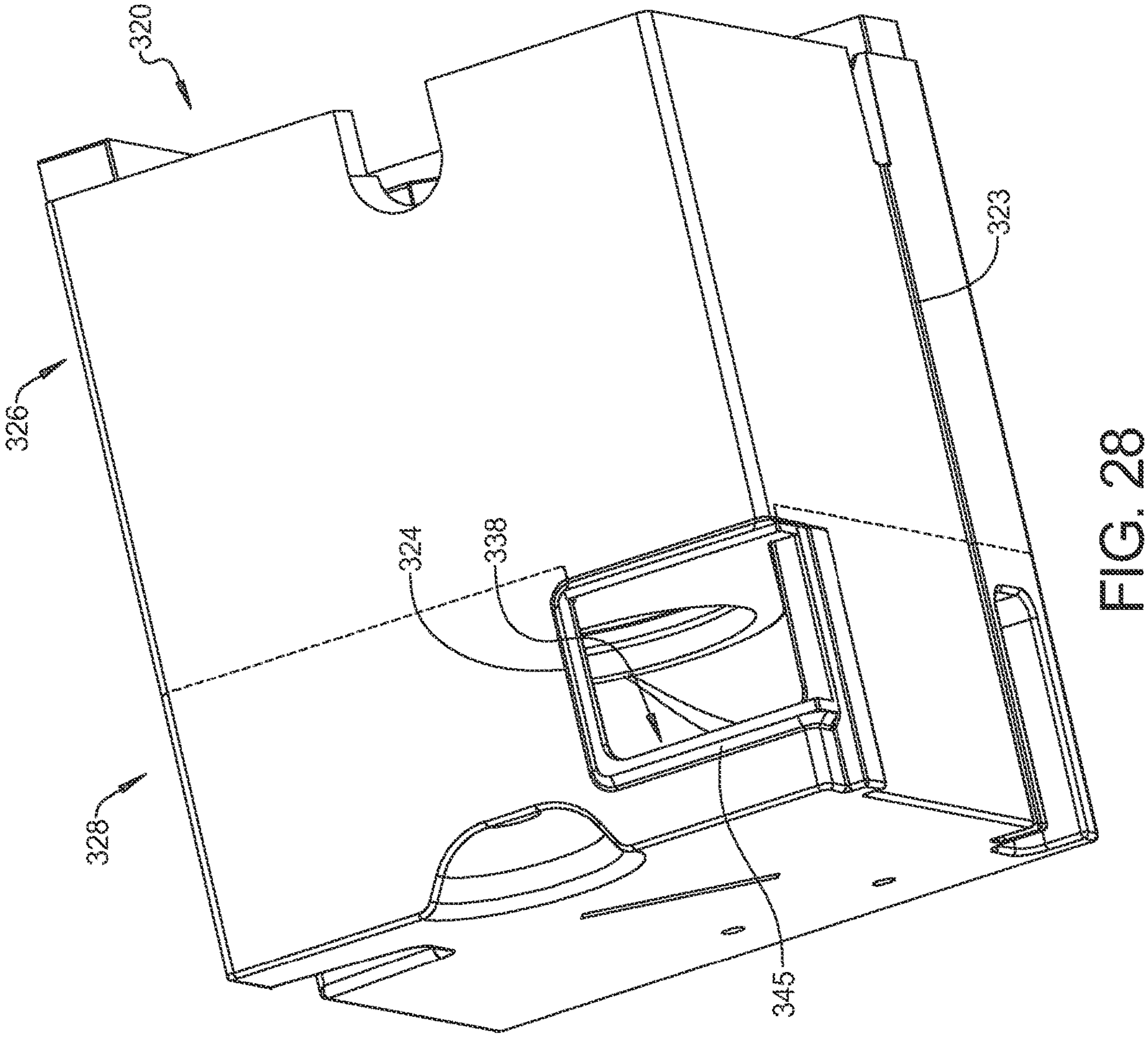
FIG. 28 is a perspective view of the two foam pieces of the sound attenuating enclosure for the smoke evacuator illustrating an enclosure outlet of the sound attenuating enclosure.

Like the sound attenuating enclosure 140, the sound attenuating enclosure 320 is at least partially formed of a material configured to attenuate noise generated by the blower assembly 306 during operation. The material may comprise any of the foam materials described above, or a different material. Additionally, geometric features can also be molded or otherwise formed in the sound attenuating disclosure 320 to accommodate electrical wires, bolts, or other components of the smoke evacuation system 300. For instance, one or more through slots may accommodate wires of the blower assembly 306. Similarly, one or more recesses or notches may be formed in the sound attenuating enclosure 320 to accommodate components of the waste collection unit 100 mounted adjacent to the sound attenuating enclosure 320. As one example, as shown in FIG. 27, a wire harness slot 323 is formed in an outer surface of the sound attenuating enclosure 320 without breaking through to an interior of the sound attenuating enclosure 320 to accommodate a wire harness.

Figure 25:
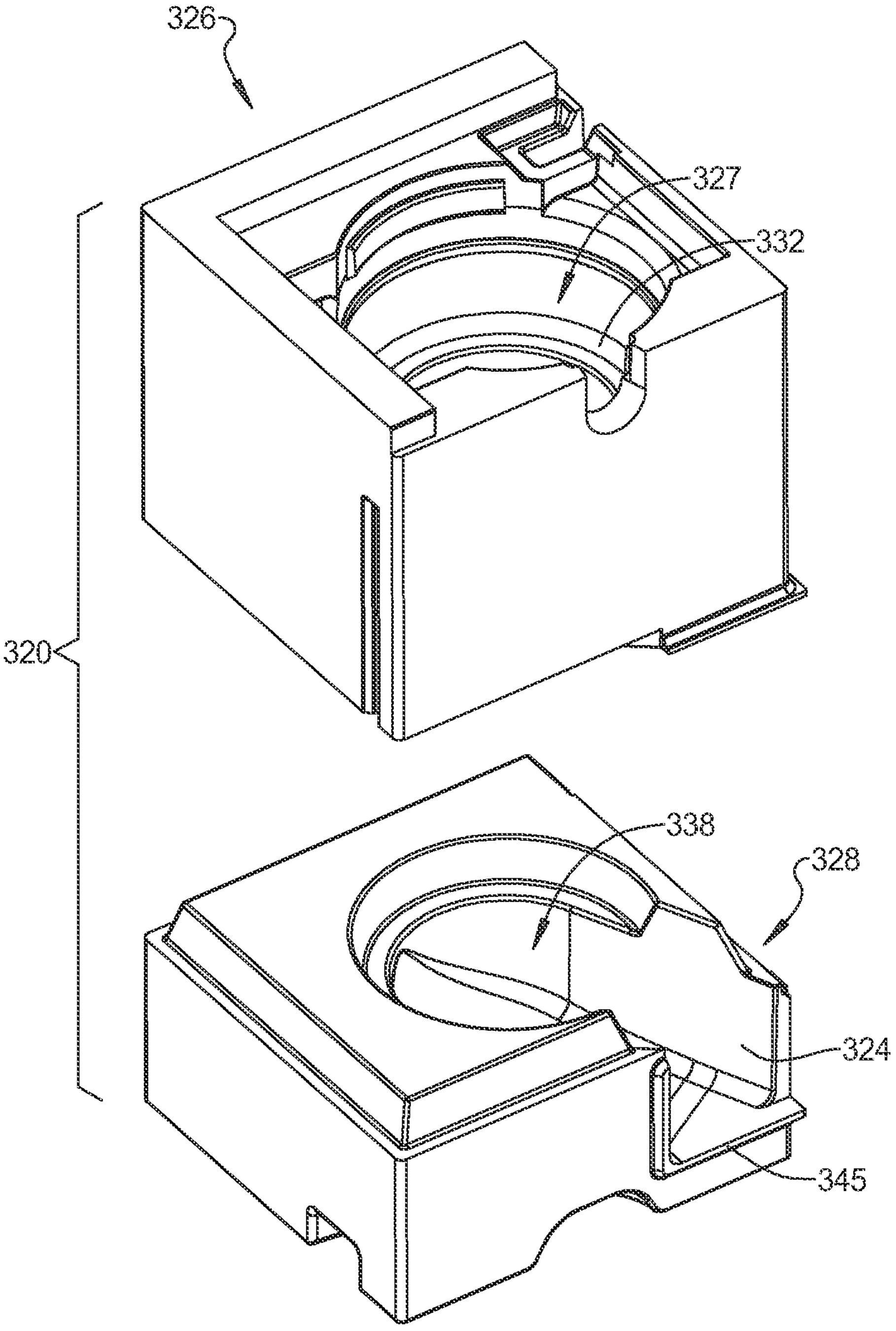
FIG. 25 is an exploded view of two foam pieces of the sound attenuating enclosure for the smoke evacuator.

The sound attenuating enclosure 320 comprises a first section 326 fixed to a second section 328. The sections 326, 328 may be connected by adhesive, ultrasonic welding, thermal welding, and the like. The sections 326, 328 are at least partially formed of sound absorbing material. In the embodiment shown in FIG. 24, the sections 326, 328 are formed entirely of foam material. In other embodiments, the sections 326, 328 may be integrally formed into a single foam piece. As shown in FIGS. 24 and 25, the sections 326, 328 may include geometrically mating features **325*a*, 325*b* to orient the sections 326, 328. The features 325*a*, 325*b* may also be asymmetrical so that the sections 326, 328 only mate in a single arrangement of the sections 326, 328**.

The first section 326 has an open first end to receive the blower assembly 306 and an open second end that opens into the second section 328. The first section 326 has a box-like exterior shape and a generally cylindrical/frustoconical inner shape, or other shape suitable for fitting to the shape of the blower motor 308 employed. The first section has a first interior region 327 shaped, in the vicinity of the motor mount 310, to generally conform to an outer surface of the motor mount 310. In particular, the first interior region 327 has a generally frustoconical shape to mate with the generally frustoconical shape of the outer surface of the motor mount 310. An annular rib 332 may be located in the first interior region 327 to frictionally engage the outer surface of the motor mount 310 and seal against the outer surface of the motor mount 310.

A second interior region 329 is adjacent to the first interior region 327. The second interior region 329 is generally cylindrically shaped to accommodate electronic components of the blower assembly 306. Owing to gaps between the electronic components and an inner surface of the first section 326, air flow paths AP are provided in the second interior region 329 to sufficiently guide the filtered air and cooling air from the inlet 319 from the second enclosure inlet 322*b* through which the filtered air and cooling air enters the sound attenuating enclosure 320, toward the open second end to enter the second section 328.

The second section 328 has an open first end to receive the filtered air passing through from the first section 326. The second section 328 extends from the open first end to a substantially closed second end, with the exception of a small slot disposed through the closed second end to accommodate wiring. The closed second end, by virtue of being substantially closed, redirects the filtered air from a longitudinal flow direction through the first section 326 to a lateral flow direction. This change in flow direction is of approximately 60-120 degrees, 80-100 degrees, or about 90 degrees and helps to further attenuate noise in the filtered air. The second section 328 directs the filtered air from the first open end to the enclosure outlet 324. The enclosure outlet 324 is formed at a junction between the first section 326 and the second section 328 in the embodiment shown.

Figure 26:
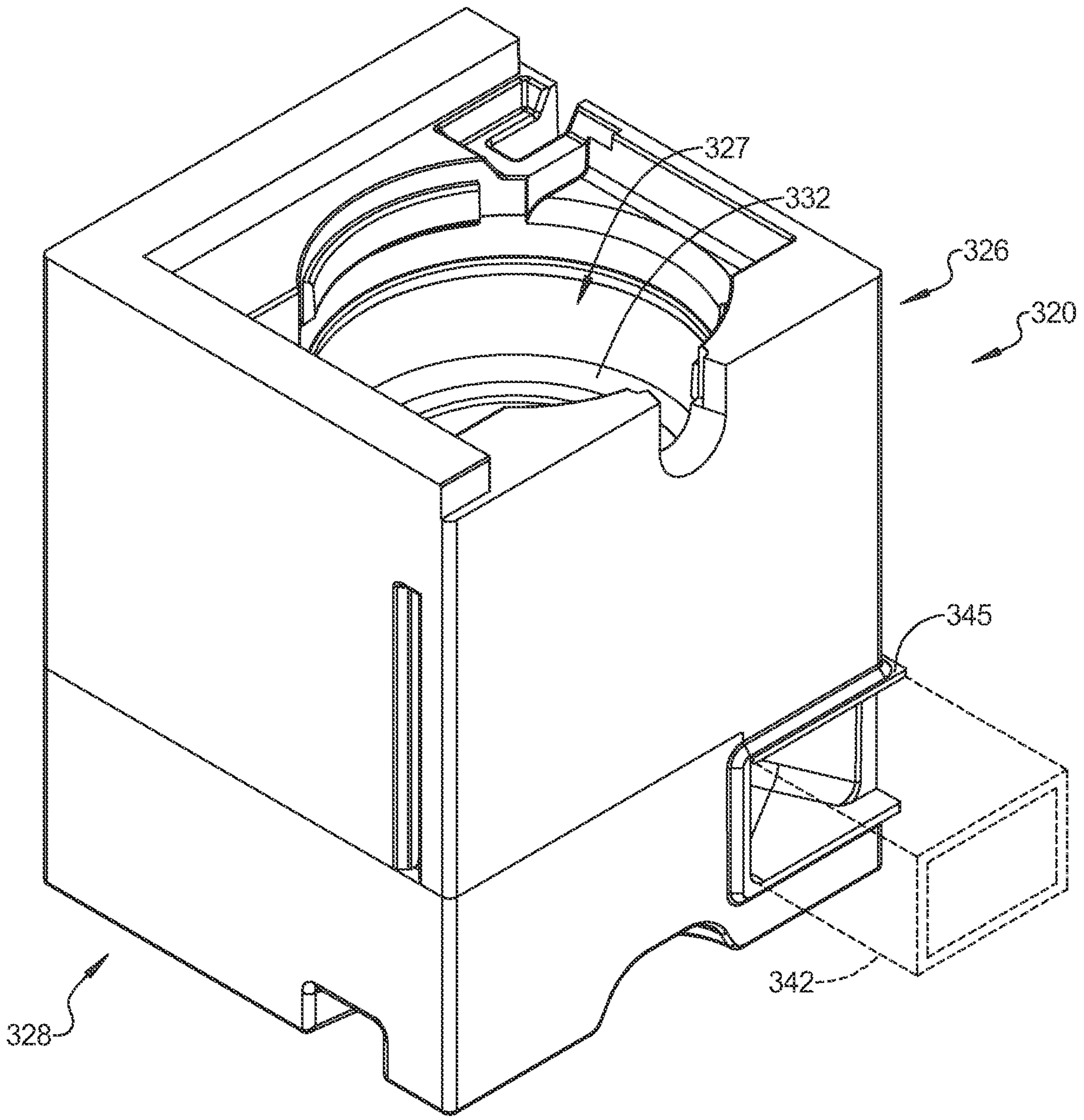
FIG. 26 is a perspective view of the two foam pieces of the sound attenuating enclosure for the smoke evacuator.

A third interior region 338 is defined between the open first end and the enclosure outlet 324 in the second section 328. The third interior region 338, as previously described, alters a flow path of the filtered air so that the filtered air is redirected from the longitudinal flow direction through the first section 326. Additionally, the third interior region 338 transitions from being partially cylindrical near the open first end to being rectangular at the enclosure outlet 324. This transition operates as an air flow chamber to gather the filtered air to be directed out of the enclosure outlet 324 and into an exhaust conduit 342 (see FIG. 26). In the embodiment shown, the exhaust conduit 342 is integrated into the chassis 112 of the waste collection unit 100, but it should be appreciated that the exhaust conduit 342 may be a separate hose or tubing in other embodiments. In the version shown, a partially peripheral lip 345 extends away from an outer surface of the second section 328 to fit to the exhaust conduit 342. The lip 345 is integrally formed with the second section 328.

Figure 15:
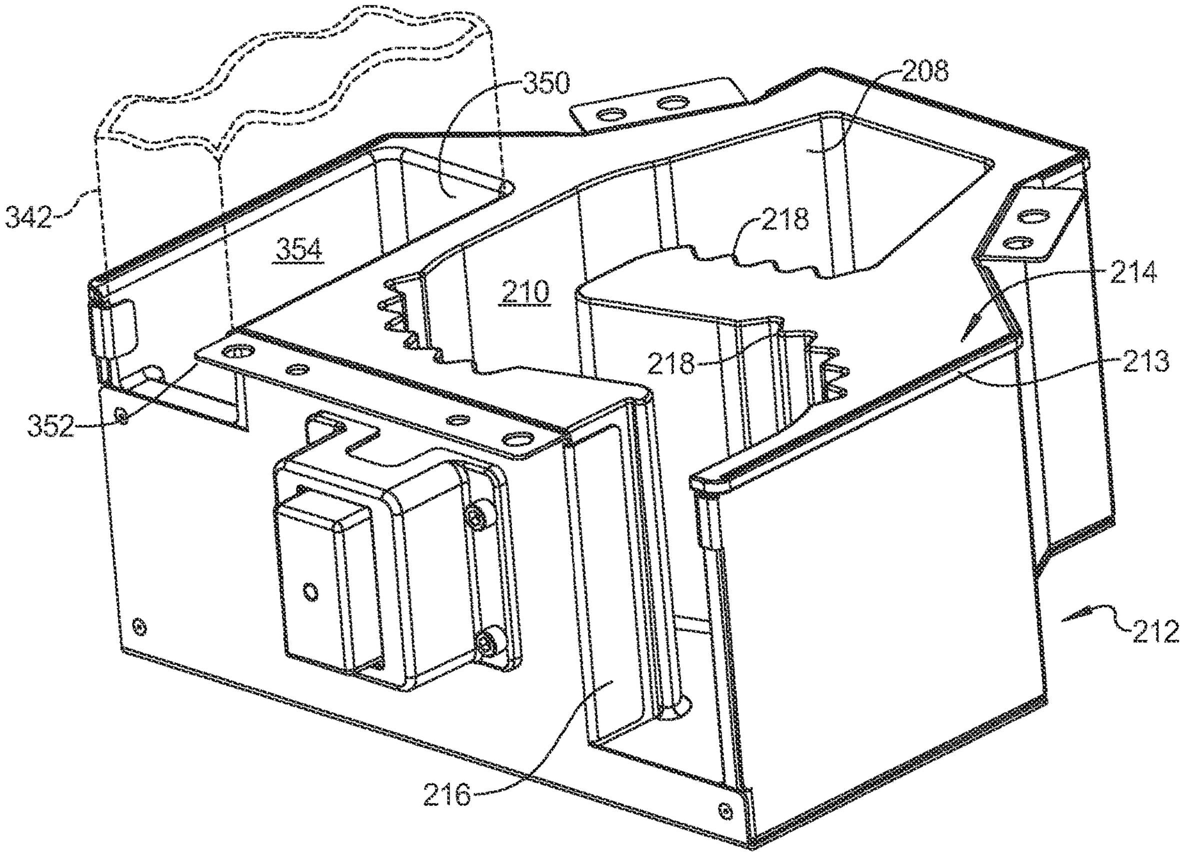
FIG. 15 is a perspective view of a plenum of the waste collection unit.
Figure 16:
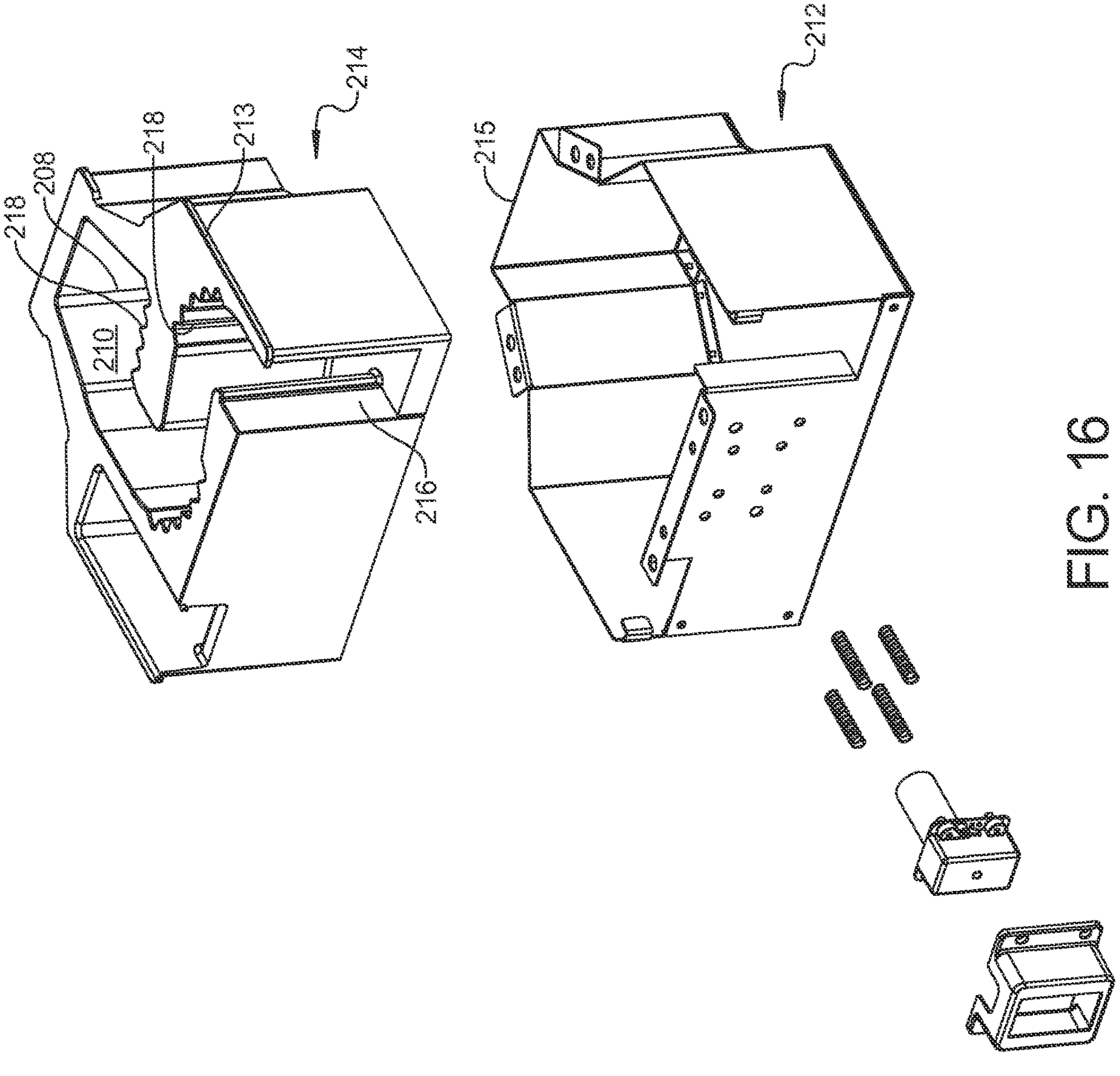
FIG. 16 is an exploded view of the plenum of FIG. 15.
Figure 17:
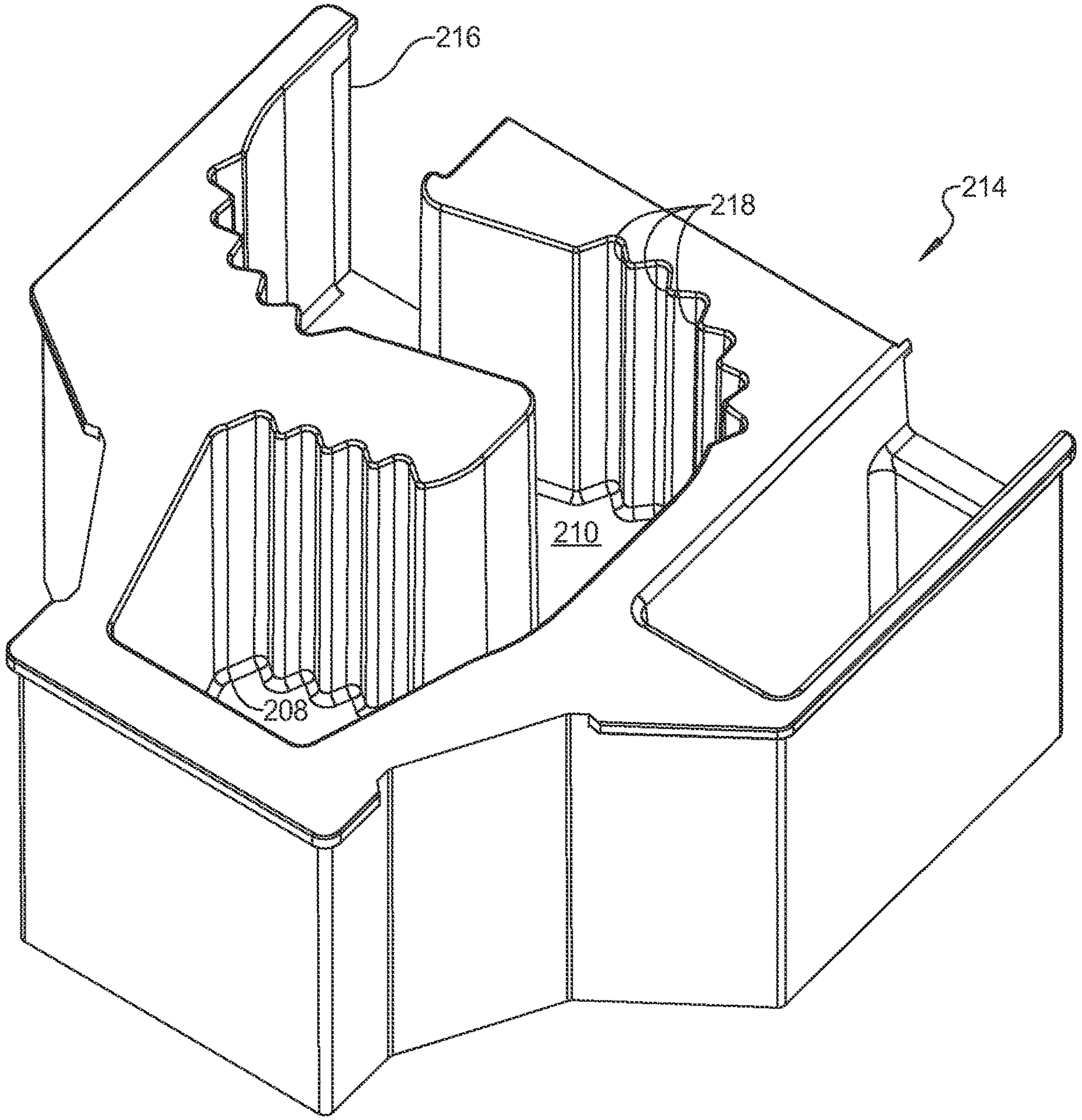
FIG. 17 is a perspective view of a foam piece of the plenum of FIG. 15.
Figure 19:
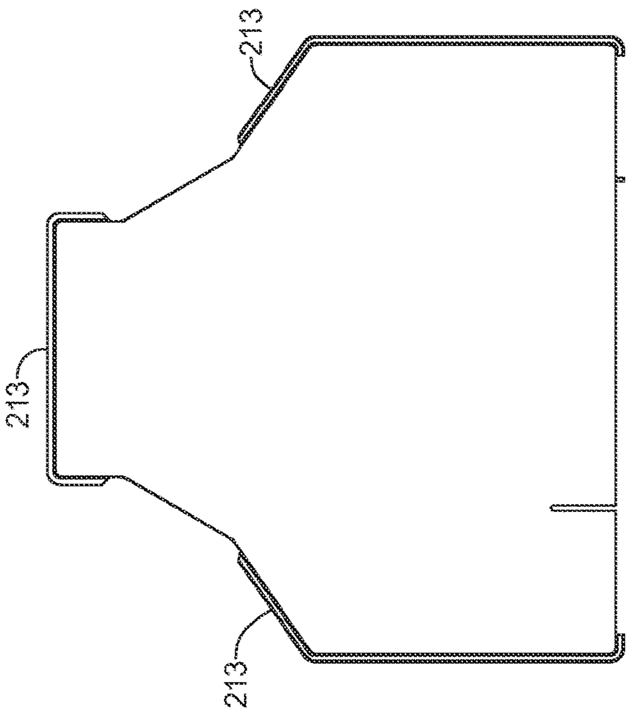
FIG. 19 is a bottom view of the foam piece of FIG. 17.
Figure 21:
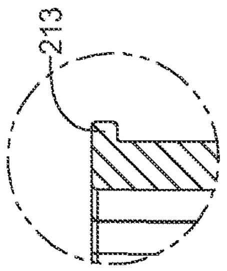
FIG. 21 is a detail view from FIG. 20.
Figure 18:
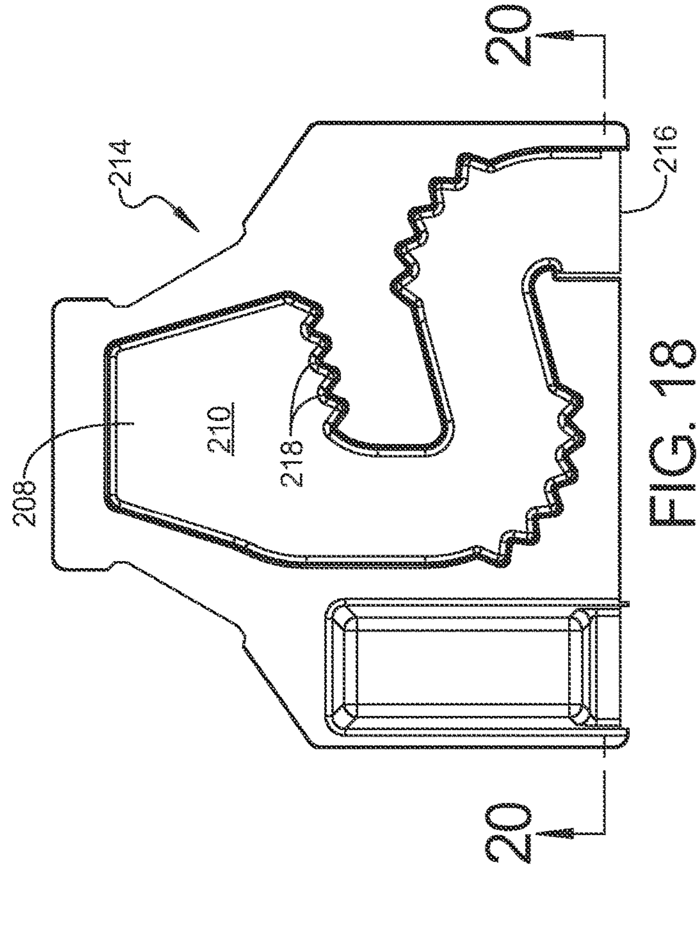
FIG. 18 is a top view of the foam piece of FIG. 17.
Figure 20:
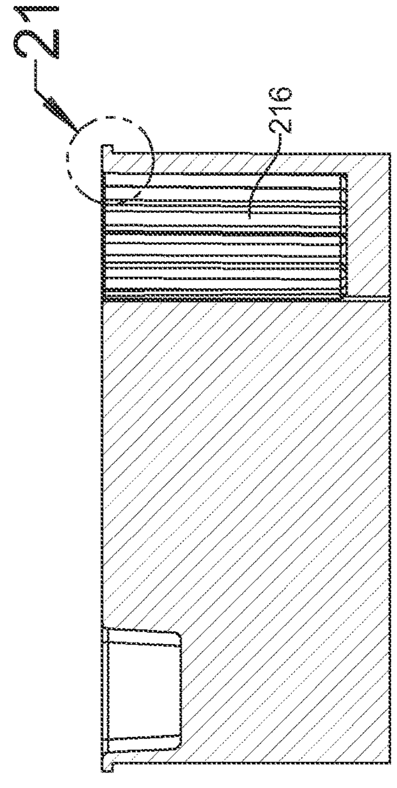
FIG. 20 is a cross-sectional view of the foam piece of FIG. 17 taken generally along the line 20-20 in FIG. 18.

The exhaust conduit 342 feeds the air that is directed from the enclosure outlet 324 into the plenum 204 at a second plenum inlet 350 (see FIG. 15). The air is then directed out of a second plenum outlet 352. The second plenum outlet 352 for the smoke evacuation system 300 is separate from the plenum outlet 216 for the sound attenuating enclosure 140. The enclosure outlet 324 of the sound attenuating enclosure 320 is in fluid communication with the second plenum inlet 350, which directs the air into a plenum chamber 354 to collect and expand the air, and then the air is directed from the second plenum outlet 352 in the same direction as the air from the plenum outlet 216. In other embodiments, the air could be directed to a separate plenum or exhausted to atmosphere from the exhaust conduit 342. In some embodiments, the exhaust conduit 342 follows a tortuous path and/or may be lined with sound absorbing material to further attenuate noise.

Figure 30:
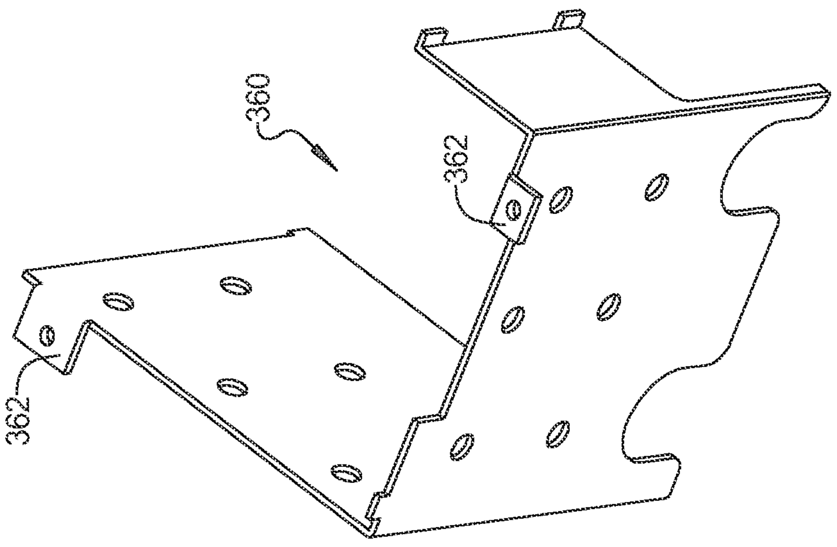
FIG. 30 is a perspective view of the noise barrier embedded in FIG. 29.
Figure 29:
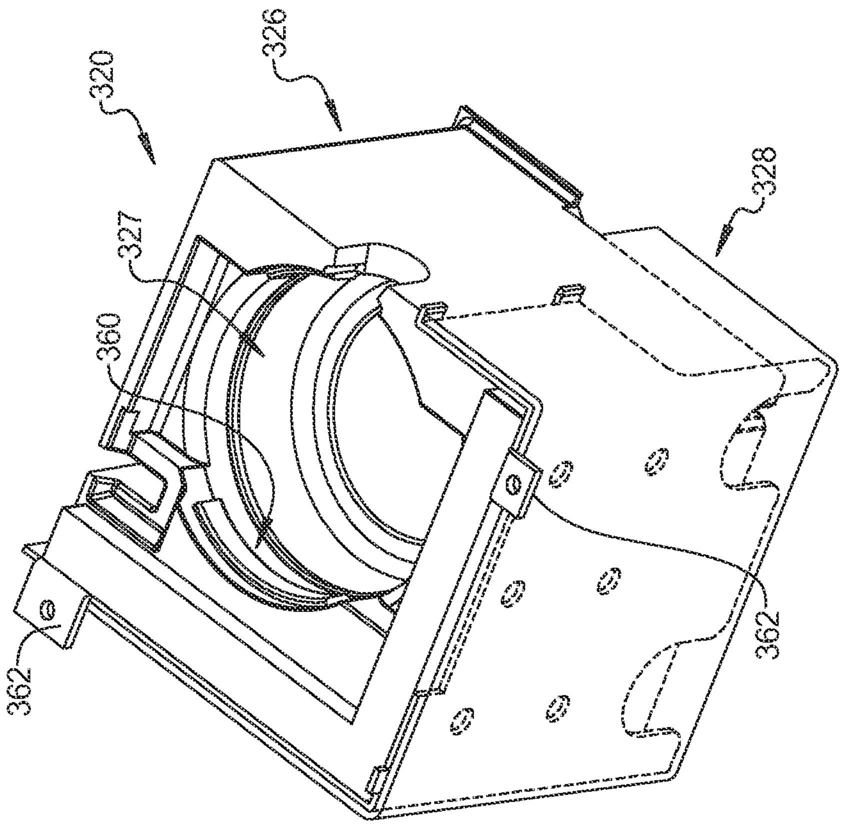
FIG. 29 is a perspective view of the two foam pieces of the sound attenuating enclosure for the smoke evacuator illustrating an embedded noise barrier.

Referring to FIGS. 29 and 30, in an alternative embodiment, the first section 326 may comprise a noise barrier 360 embedded in the foam material. The foam material may be molded around the noise barrier 360. The noise barrier 360 comprises at least one of metal and plastic, and may be flexible or rigid. The noise barrier 360 may be formed of aluminum to redirect any sound coming out of the first section 326 back into the first section 326. The noise barrier 360 may be solid or have openings to facilitate being embedded in the foam material. The noise barrier 360 may have exposed mounting brackets 362 to facilitate mounting of the first section 326 and the entire sound attenuating enclosure 320 to the chassis 112 of the waste collection unit 100, to the filter housing 307, or to other components. The noise barrier 360 may be formed of several pieces or a single piece of material.

Figure 30A:
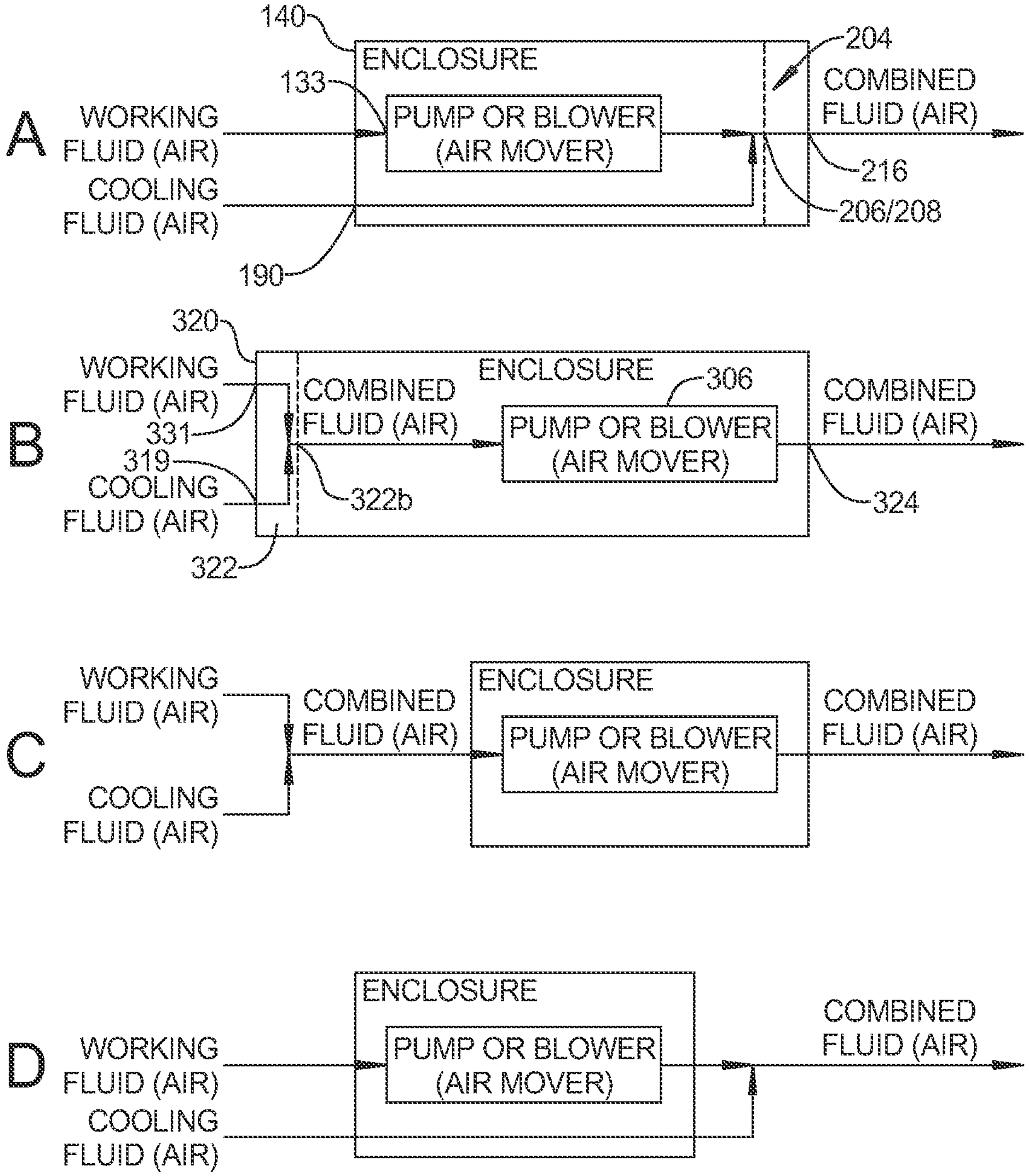
FIG. 30A is an illustration of various sound attenuating enclosure configurations.

Other possible arrangements of the sound attenuating enclosures 140, 320 are also contemplated. Referring to FIG. 30A, four possible configurations of enclosures are shown in which working fluid (e.g., working air) is combined with cooling fluid (e.g., cooling air) in four scenarios: Example A in which working fluid is combined with cooling fluid inside the enclosure, but downstream of an air mover such as a pump or blower; Example B in which the working fluid and the cooling fluid are combined inside the enclosure, but upstream of the air mover; Example C in which the working fluid and the cooling fluid are combined upstream of the enclosure; and Example D in which the working fluid and the cooling fluid are combined downstream of the enclosure. The embodiments of the sound attenuating enclosure 140 shown in the preceding figures fall within Example A, as indicated by the accompanying numerals, but it should be appreciated that the sound attenuating enclosure 140 could be configured in accordance with any of Examples A-D. The embodiments of the sound attenuating enclosure 320 shown in the preceding figures fall within Example B, as indicated by the accompanying numerals, but it should be appreciated that the sound attenuating enclosure 320 could be configured in accordance with any of Examples A-D.

Figure 31:
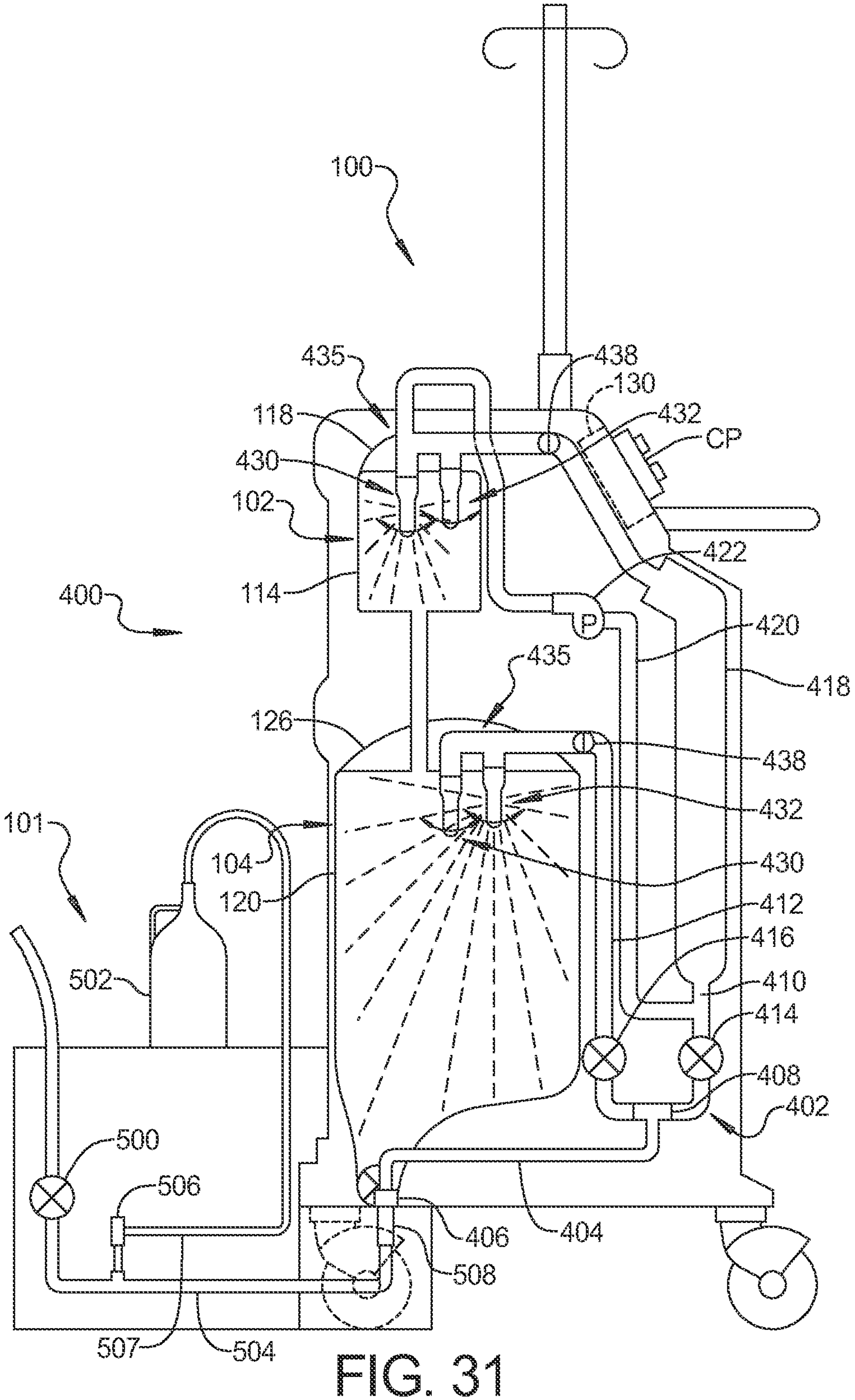
FIG. 31 is a schematic illustration of a cleaning system of the waste collection unit.

Referring to FIG. 31, a cleaning system 400 is supported on-board the waste collection unit 100 for cleaning the waste collection unit 100. The cleaning system 400 includes a cleaning circuit 402 of water lines and associated flow components supported on the waste collection unit 100, as described below.

The cleaning circuit 402 comprises a supply line 404 that extends from a water coupling 406 on the waste collection unit 100 to a tee 408. The water coupling 406 is configured to receive pressurized water from a water source, as described further below, to supply water for the cleaning circuit 402 during cleaning. From the tee 408, the supply line 404 is split into an upper supply line 410 and a lower supply line 412. The lower supply line 412 includes an electronically operated lower solenoid valve 416. The lower solenoid valve 416 controls the flow of liquid into the lower waste container 104. The upper supply line 410 includes a matching electronically operated upper solenoid valve 414 to control the flow of liquid into the upper waste container 102.

The upper supply line 410 opens into an on-board reservoir 418 for storing water to provide prefill, as described in U.S. Pat. No. 7,621,898, hereby incorporated by reference herein. The upper supply line 410 continues to the upper cap

118 of the upper waste container 102. A secondary supply line 420 splits flow from the upper supply line 410, just below the on-board reservoir 418. A first end of the secondary supply line 420 is located below the on-board reservoir 418 with respect to gravity to be able to drain the on-board reservoir 418 during use. A second end of the secondary supply line 420 empties into the upper waste container 102. A prefill pump 422 conveys the stored water from the on-board reservoir 418 through the secondary supply line 420 into the upper waste container 102 during use to provide a desired tare volume of liquid in the upper canister 114. The prefill pump 422 automatically pumps a predetermined amount of liquid into the upper canister 114 after each time the upper waste container 102 is dumped into the lower waste container 104 and after each cleaning. The prefill pump 422 is controlled by a prefill controller (not shown) in communication with the main controller 130. It should be appreciated that the cleaning circuit 402 could assume other configurations in other embodiments. For instance, in some versions only a single waste container is employed to collect waste materials.

Figure 32:
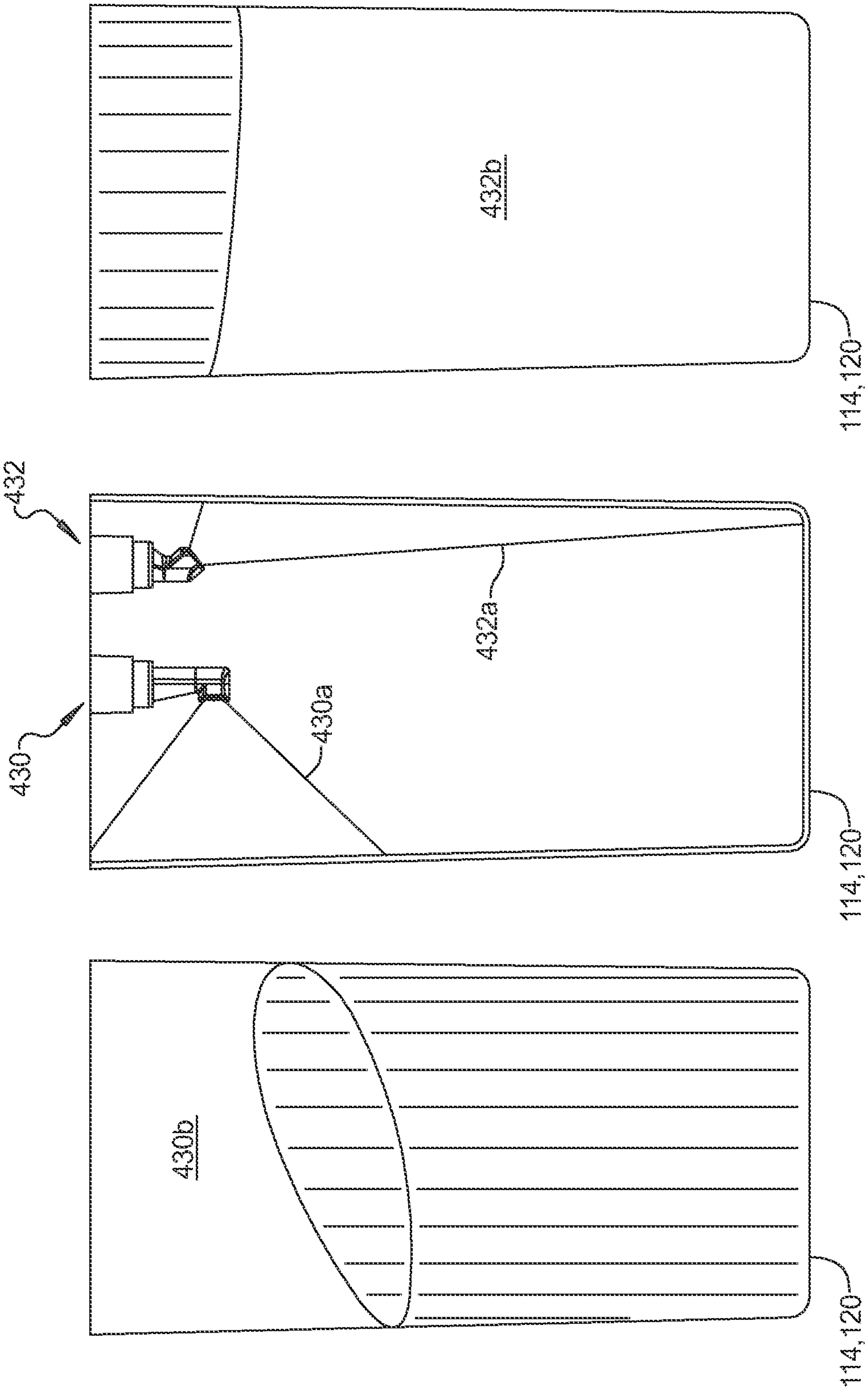
FIG. 32 is an illustration of two liquid delivery devices of the cleaning system of FIG. 31 and their scope of surface coverage on a waste container.
Figure 33:
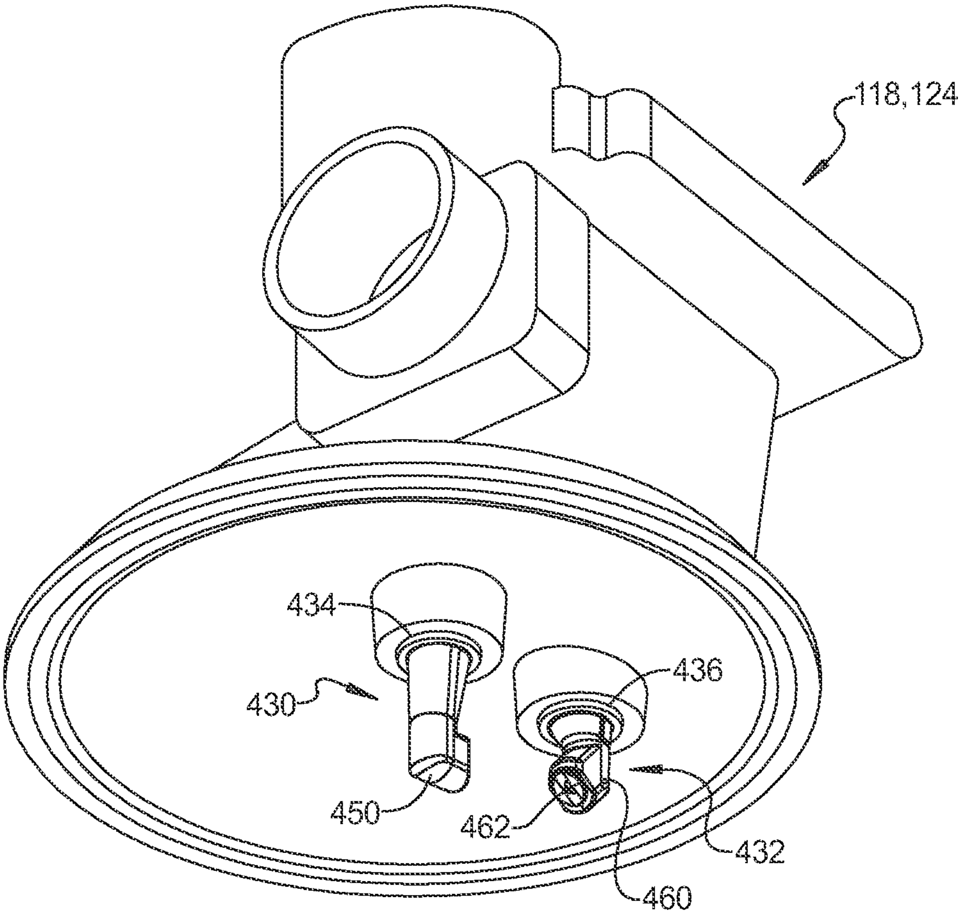
FIG. 33 is an exploded view of a cap assembly incorporating parts of the cleaning system.

Referring to FIGS. 31-33, two liquid delivery devices 430, 432, such as sprinklers, are provided in each waste container 102, 104 to clean the waste containers 102, 104. The liquid delivery devices 430, 432 are arranged to rotate in the waste containers 102, 104 to direct liquid onto the internal surfaces of the waste containers 102, 104, which include internal surfaces of the canisters 114, 120. In other embodiments, more or fewer liquid delivery devices may be used.

As shown in FIG. 32, by virtue of their rotation in the waste containers 102, 104, the liquid delivery devices 430, 432 are able to cover the entire internal surface of a side wall of the canisters 114, 120. This is accomplished by the spray fan patterns 430*a*, 432*a*, shown for each of the liquid delivery devices 430, 432 and the resulting coverage patterns 430*b*, 432*b* shown on the canisters 114, 120. The liquid delivery devices 430, 432 shown have different geometric configurations and spray patterns 430*a*, 432*a*, but in other embodiments, the liquid delivery devices 430, 432 may have the same configuration and spray patterns.

Figure 34:
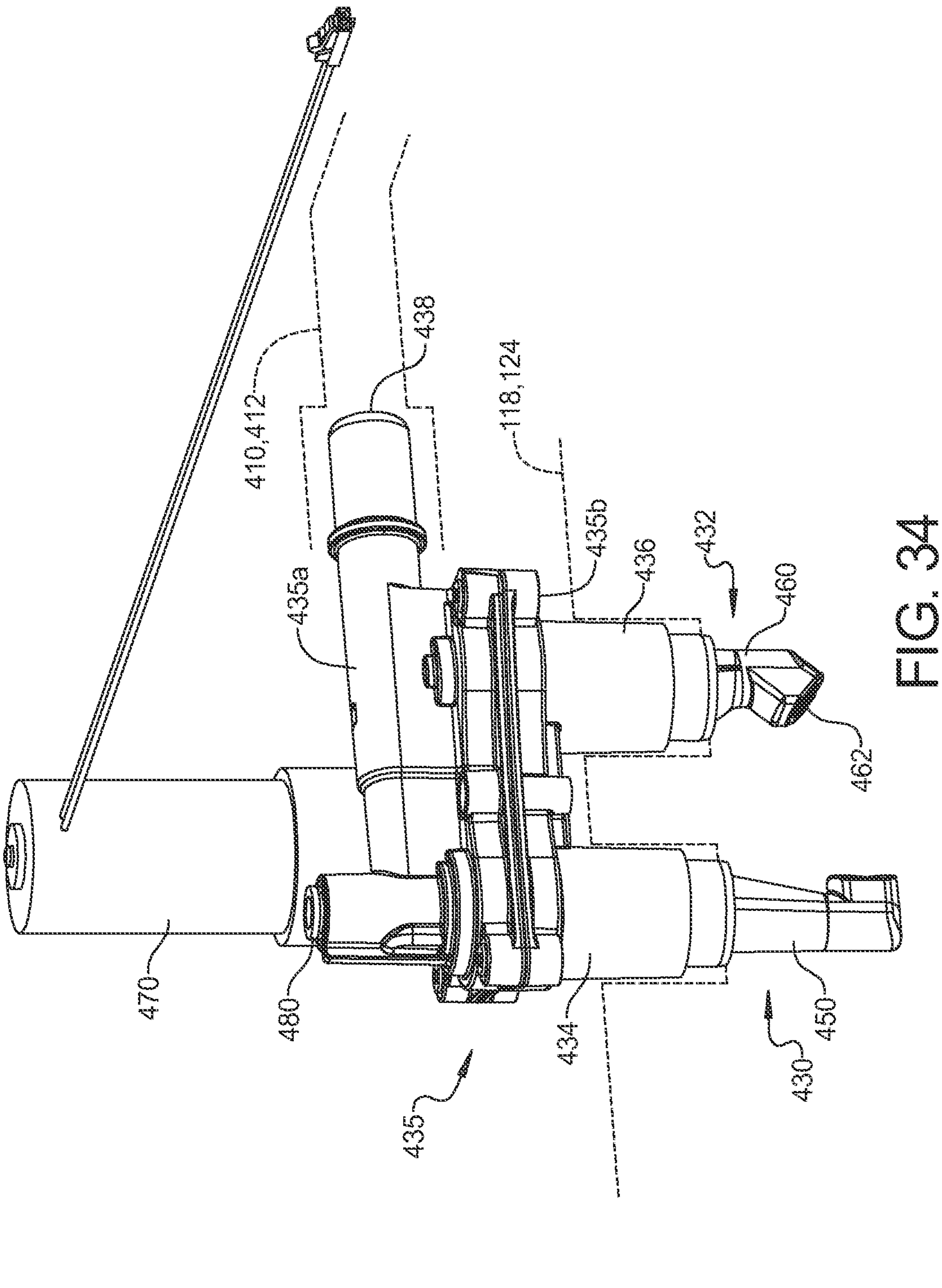
FIG. 34 is a perspective view of a manifold, the liquid delivery devices, and an actuator of the cleaning system.
Figure 35:
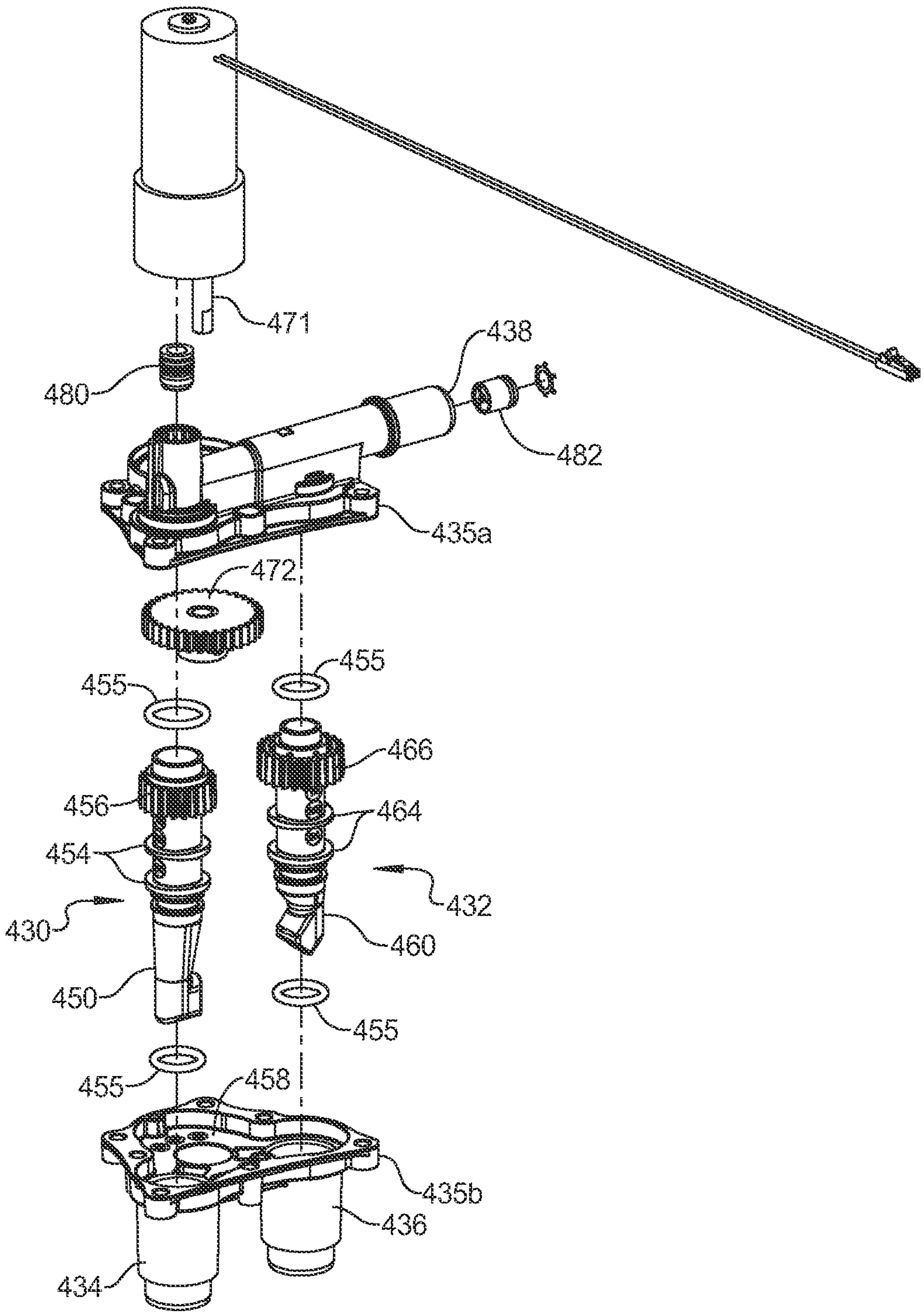
FIG. 35 is an exploded view of the manifold, the liquid delivery devices, and the actuator of FIG. 34.
Figure 36:
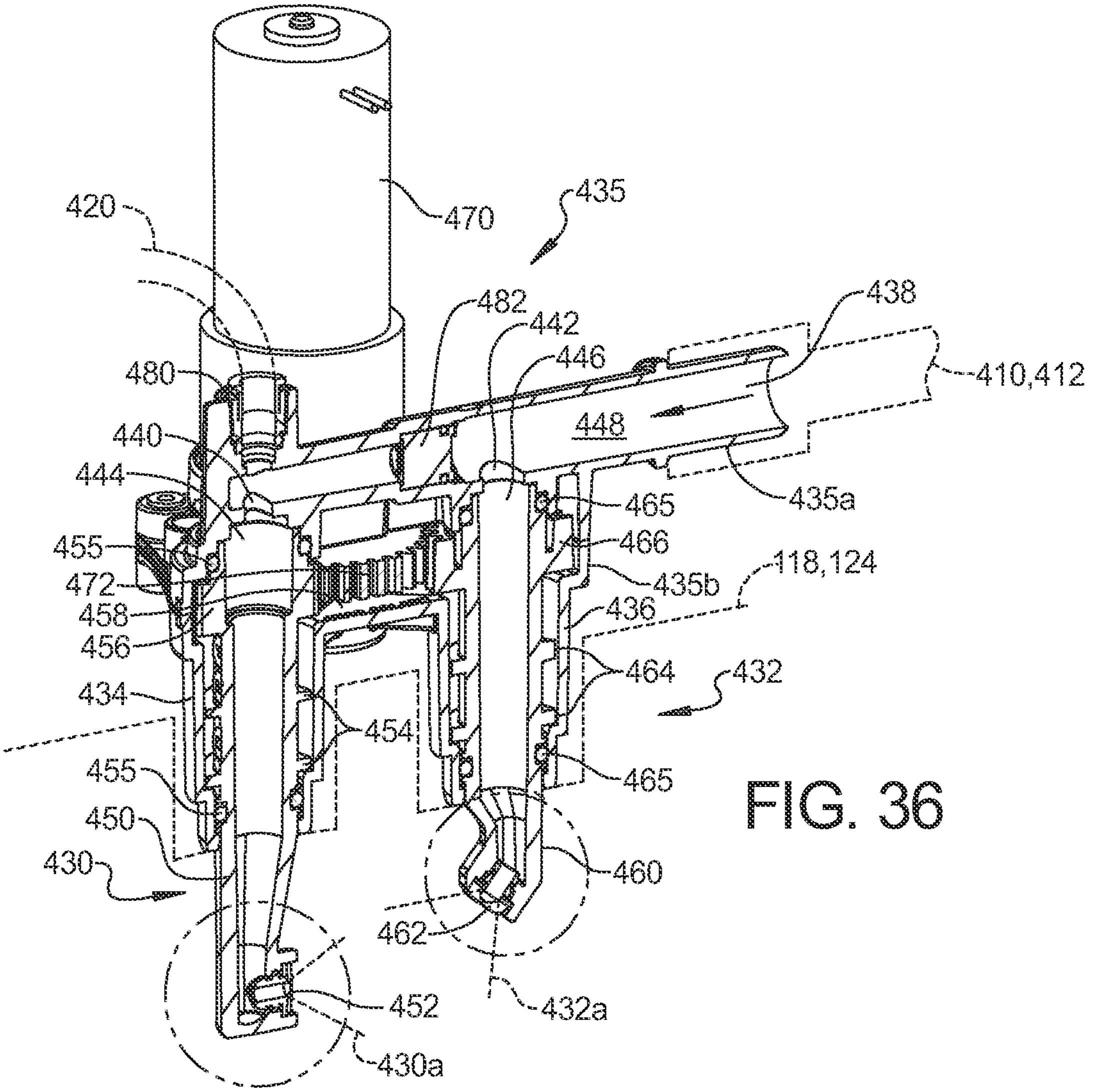
FIG. 36 is a cross-sectional view of the manifold and liquid delivery devices of FIG. 34.

Referring to FIGS. 34-36, the liquid delivery devices 430, 432 are rotatably mounted in a manifold 435. More specifically, the liquid delivery devices 430, 432 are rotatably mounted in ports 434, 436 of the manifold 435. The liquid delivery devices 430, 432 are mounted so that they are able to rotate relative to the waste containers 102, 104, but are fixed from axially moving relative to the waste containers 102, 104.

The manifold 435 is mounted to the caps 118, 124 of the waste containers 102, 104. The distal end of the upper supply line 410 is connected to an inlet 438 of the manifold 435 in fluid communication with the liquid delivery devices 430, 432 located in the upper waste container 102. The distal end of the lower supply line 412 is connected to an inlet 438 of a separate manifold 435 in fluid communication with the liquid delivery devices 430, 432 located in the lower waste container 104. These distal ends define outlets to convey cleaning liquid to the liquid delivery devices 430, 432 via the manifolds 435.

Referring to FIG. 36, the manifolds 435 direct liquid, such as water and cleaner, from the supply lines 410, 412 to the liquid delivery devices 430, 432. Each manifold 435 further comprises a pair of openings 440, 442 that open into the ports 434, 436. Once through the openings 440, 442, the liquid enters the liquid delivery devices 430, 432. More specifically, the liquid delivery devices 430, 432 have open proximal ends defining openings 444, 446 through which the liquid enters into the liquid delivery devices 430, 432. The manifold 435 further comprises a main flow passage 448 to carry the liquid from the inlet 438 to the openings 440, 442. The manifold 435 shown comprises first and second manifold sections 435*a*, 435*b* fastened together to capture the liquid delivery devices 430, 432 therebetween.

The first liquid delivery device 430 comprises an elongated tube 450 that extends from an open proximal end to an open distal end. The elongated tube 450 is generally cylindrical in shape, but could be formed in other shapes. The open distal end of the elongated tube 450 extends beyond an open distal end of the port 434. A first spray nozzle 452 is mounted in the open distal end of the elongated tube 450 to provide the spray pattern 430*a*. The first nozzle 452 may be fixed in the distal end by threading, adhesive, press-fit, and the like. The first nozzle 452 may also be replaceable during servicing or interchangeable with different nozzles to create different spray patterns for certain applications. In the embodiment shown, the first nozzle 452 is configured to discharge the first spray pattern 430*a* at a spray angle subtended by the first spray pattern 430*a*. The spray angle may be from 0-50 degrees, at least 50 degrees, from 60-100 degrees, from 70-90 degrees, or about 80 degrees. As shown in FIG. 32, the first nozzle 452 is configured to discharge the first spray pattern 430*a* at an upper portion of the internal surface of the waste containers 102, 104. The first nozzle 452 may be configured to provide a flat spray pattern, a cone spray pattern, a hollow cone spray pattern, or other spray patterns.

A pair of spaced, annular ribs 454 are located on an outer surface of the elongated tube 450 to rotatably support the elongated tube 450 for rotation in the port 434. Additionally, dynamic and/or o-ring seals 455 are located in an outer groove and adjacent the open proximal end of the elongated tube 450 to seal against the port 434.

A first gear 456 is located adjacent the open proximal end of the elongated tube 450, below one of the seals 455, to facilitate rotation of the first liquid delivery device 430, as described further below. The first gear 456 is located in a gear train chamber 458 of the manifold 435. The ribs 454 and the first gear 456 are shown as being integrally formed with the elongated tube 450, but could be separate parts fixed together in a conventional manner.

The second liquid delivery device 432 has a similar, but slightly different configuration than the first liquid delivery device 430. In other embodiments, the second liquid delivery device 432 may have the same configuration as the first liquid delivery device 430. The second liquid delivery device 432 comprises an elongated tube 460 that extends from an open proximal end to an open distal end. The elongated tube 460 is generally cylindrical in shape, but could be formed in other shapes. The open distal end of the elongated tube 460 extends beyond an open distal end of the port 436. A second spray nozzle 462 is mounted in the open distal end of the elongated tube 460 to provide the spray pattern 432*a*. The second nozzle 462 may be fixed in the distal end by threading, adhesive, press-fit, and the like. The second nozzle 462 may also be replaceable during servicing, or interchangeable with different nozzles to create different spray patterns for certain applications. In the embodiment shown, the second nozzle 462 is configured to discharge the second spray pattern 432*a* at a spray angle subtended by the second spray pattern 432*a*. The spray angle may be from 0-50 degrees, at least 50 degrees, from 50-90 degrees, from 60-80 degrees, or about 70 degrees. As shown in FIG. 32, the second nozzle 462 is configured to discharge the second spray pattern 432*a* at mid-to-lower portions of the internal surface of the waste containers 102, 104. The second nozzle 462 may be configured to provide a flat spray pattern, a cone spray pattern, a hollow cone spray pattern, or other spray patterns.

Figure 36A:
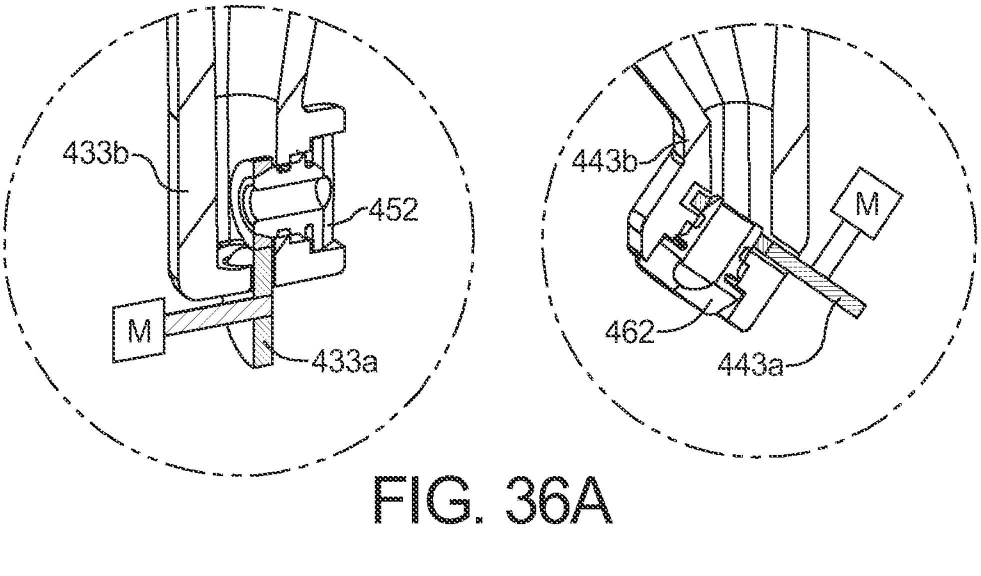
FIG. 36A is a cross-sectional views of nozzles with separate motors for rotating the nozzles.

The nozzles 452, 462 are configured to discharge spray patterns 430*a*, 432*a* that impact the internal surfaces of the waste containers 102, 104 at different locations. In alternative embodiments, like that shown in FIG. 36A, the nozzles 452, 462 may also be configured to rotate about a central nozzle axis during operation so that their spray patterns rotate about the nozzle axis. As shown, motors M may be used to rotate drive members 433*a*, 443*a*, such as drive gears, that in turn rotate driven gears 433*b*, 443*b* that are fixed to the nozzles 452, 462. In these embodiments, the motors M may be supported by the tubes 450, 460 in separate housings (not shown) to protect the motors M.

A pair of spaced, annular ribs 464 are located on an outer surface of the elongated tube 460 to rotatably support the elongated tube 460 for rotation in the port 436. Additionally, dynamic and/or o-ring seals 465 are located in an outer groove and adjacent the open proximal end of the elongated tube 460 to seal against the port 436.

A second gear 466 is located adjacent the open proximal end of the elongated tube 460, below one of the seals 465, to facilitate rotation of the second liquid delivery device 432, as described further below. The second gear 466 is located in the gear train chamber 458 of the manifold 435. The ribs 464 and the second gear 466 are shown as being integrally formed with the elongated tube 460, but could be separate parts fixed together in a conventional manner.

Figure 37:
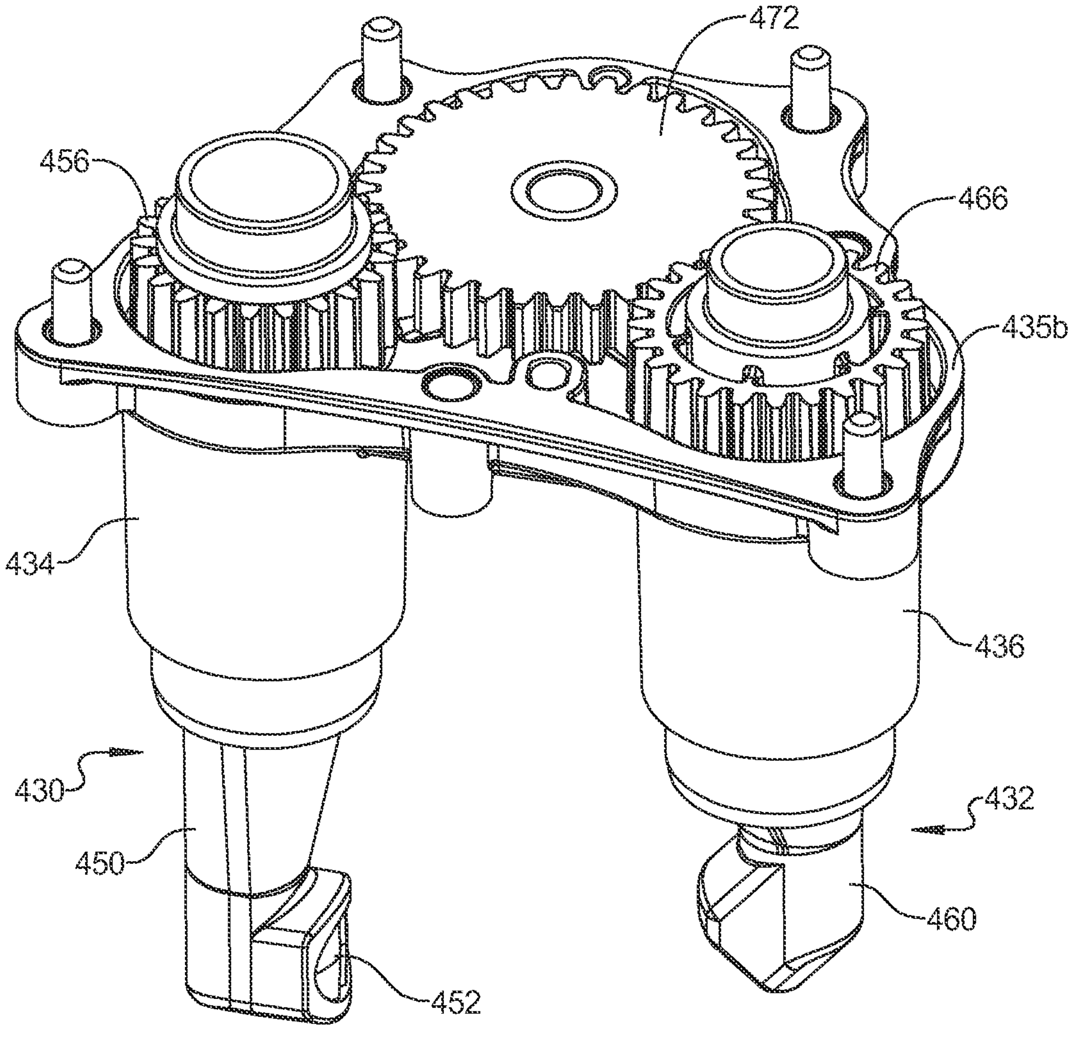
FIG. 37 is a perspective view of a gear arrangement for the two liquid delivery devices.

An electrically-powered actuator 470 is operatively coupled to each set of the liquid delivery devices 430, 432 for rotating the liquid delivery devices 430, 432 relative to the waste containers 102, 104 to direct liquid on the internal surfaces. In the embodiment shown, each actuator 470 comprises a motor mounted to the manifold 435. The actuators 470 are thus supported by the caps 118, 124. Each motor has a drive shaft 471 (see FIG. 35) that rotates a drive gear 472 disposed for rotation in the gear train chamber 458 of the manifold 435. The motor rotates the drive gear 472, which in turn rotates the first and second gears 456, 466 (see FIG. 37). In some embodiments, the gears are arranged so that the liquid delivery devices 430, 432 rotate in the same direction, while in other embodiments, the gears are arranged so that the liquid delivery devices 430, 432 rotate in opposite directions. In further embodiments, separate actuators 470 may be directly connected to the liquid delivery devices 430, 432 without intermediate gears.

Each actuator 470 is in communication with the main controller 130 to be controlled by the main controller 130 during cleaning operations. The actuators 470 may be constant or variable speed and/or may be reversible. The gear arrangement operatively couples the actuators 470 to the liquid delivery devices 430, 432 so that the liquid delivery devices 430, 432 rotate at different rotational speeds. In particular, the first and second gears 456, 466 may have a different number of gear teeth and different diameters so that the first and second gears 456, 466 rotate at different rotational speeds. By rotating at different speeds, the nozzles 452, 462 are configured so that the spray patterns 430*a*, 432*a* don't cross in the same space, and in the same manner, for each rotation, thereby preventing shadows on the canisters 114, 120.

In other embodiments, separate actuators 470 could be employed for each of the liquid delivery devices 430, 432 to enable rotation of the liquid delivery devices 430, 432 at different speeds, to allow one of the liquid delivery devices 430, 432 to rotate while the other is stationary, to rotate the liquid delivery devices 430, 432 in different rotational directions, or any combination of these functions or other functions enabled by providing separately controllable actuators 470.

When using the actuator 470 to rotate the liquid delivery devices 430, 432, all available water pressure from the pressurized water source is used to generate cleaning power, not to rotate the liquid delivery devices 430, 432. It should be appreciated, however, that in other embodiments, some of the water pressure could be used to rotate the liquid delivery devices 430, 432. The actuators 470 also provide the benefit of being able to control the rotational speeds of the liquid delivery devices 430, 432. In some cases, it may be necessary to slow the rotational speeds to concentrate spray on smaller areas of the canisters 114, 120. This could be controlled automatically by the main controller 130 or by user input on the control panel CP.

Current sensors may be in communication with the actuators 470 and the main controller 130 for monitoring current drawn by the motors and detecting whether the motors are in a stalled condition. This could be used to sense an open motor.

Figure 38:
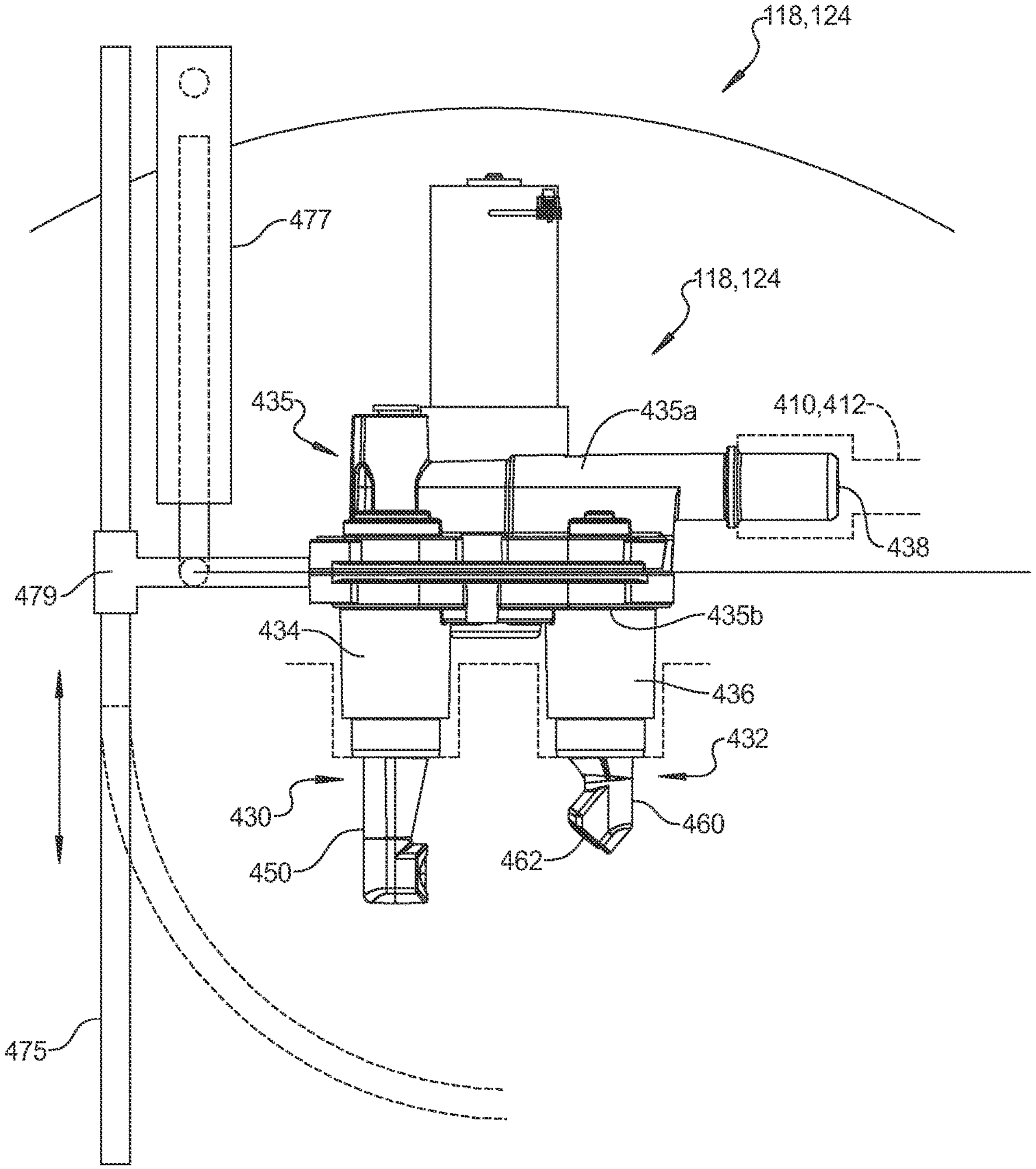
FIG. 38 is a partially perspective and partially schematic view of a linear actuator used to linearly move the manifold.

In other embodiments, the liquid delivery devices 430, 432 may be able to move both rotationally and axially relative to the waste containers 102, 104. For instance, referring to FIG. 38, the manifolds 435 are able to slide relative to their associated caps 118, 124, such as along a track or rail 475 attached to the caps 118, 124. As a result, only one of the liquid delivery devices 430, 432 may be needed in each of the waste containers 102, 104 to clean the entire internal surfaces of the waste containers 102, 104, particularly if the single liquid delivery device is able to be positioned vertically halfway in the waste containers 102, 104. In these cases, linear actuators 477 may be operatively connected to each of the manifolds 435 via a carrier 479 fixed to each of the manifolds 435. The carriers 479 are configured to slide along their respective rails 475.

Housings of the linear actuators 477 and the rails 475 along which the carriers 479 slide are fixed to the caps 118, 124. The linear actuators 477 have linearly movable drive rods that extend and retract relative to their housings to raise and lower the manifolds 435 relative to the caps 118, 124 via the carriers 479. Distal ends of the drive rods are fixed to the carriers 479. The linear actuators 477 are controlled by the main controller 130 in the same manner as discussed above for the actuators 470. Other configurations for providing axial movement of the liquid delivery devices 430, 432 are also contemplated, including actuators that only move one or both of the liquid delivery devices 430, 432, and not the entire manifold 435.

In further embodiments, the manifold 435, or the liquid delivery devices 430, 432, may be able to articulate about a pivot axis arranged horizontally in the waste containers 102, 104 or may otherwise be configured to be re-oriented horizontally (or at least partially out of their normally vertical orientation) in the waste containers 102, 104. In these cases, only one of the liquid delivery devices 430, 432 may be needed. In one embodiment, the tracks or rails 475 along which the manifolds 435 descend into the waste containers 102, 104 could be arcuate in shape so that as the manifolds 435 descend further into the waste containers 102, 104, the manifolds 435 follow an arcuate path that re-orients the manifolds 435 (see hidden lines in FIG. 38). In this case, the housings of the linear actuators 477 are pivotally connected to the caps 118, 124 and the distal ends of the drive rods are pivotally connected to the carriers 479 to allow such arcuate movement (see hidden pivot connections in FIG. 38).

The manifold 435 may further comprise a prefill port 480 in communication with the main flow passage 448 to receive the secondary supply line 420 so that prefill liquid from the on-board reservoir 418 can be delivered into the manifold 435 via the prefill pump 422. A one-way check valve 482 is located in the main flow passage 448 to separate the openings 440, 442, so that when the prefill liquid is being delivered into the manifold 435 via the prefill pump 422, the prefill liquid is only able to flow into the opening 440 and not the opening 442. Accordingly, the prefill liquid enters the upper waste container 102 via the liquid delivery device 430 only and not the liquid delivery device 432. In other embodiments, the prefill liquid may be delivered through both of the liquid delivery devices 430, 432.

In operation, referring back to FIG. 3, the waste collection unit 100 is wheeled to a use area, e.g., an operating room, to be used in a medical procedure such as a knee surgery. One or more of the suction lines S are connected to one or more inlets on the disposable manifolds M. When an input on the control panel CP is used to activate the vacuum pump 132, the vacuum pump 132 begins to draw a selectively variable vacuum within one or more of the waste containers 102, 104, which causes a vacuum to be pulled through the suction lines S drawing in the waste material through the connected suction lines S. The control panel CP is used to set the desired vacuum levels in the waste containers 102, 104.

Referring to FIG. 31, once both the upper and lower canisters 114, 120 are filled, or if the user desires to empty and clean the waste containers 102, 104 prior to being filled, the user wheels the waste collection unit 100 to the docking station 101 to off-load the waste material to the waste drain and clean the waste containers 102, 104.

The cleaning system 400 can be activated after the waste material has been off-loaded from the waste collection unit 100 to the waste drain or for other disposal. Once this occurs, cleaning occurs based on the user desired level of cleaning. This can be accomplished by selecting a dial position, pressing a pushbutton, selecting a touch screen button etc., on the control panel CP. The user may select between a “quick clean” option, a “normal clean” option, and an “extended clean” option. The user’s selection is transmitted via a control signal to the main controller 130, which then instructs a docking controller (not shown) on the docking station 101 to act accordingly. Cleaning of the waste containers 102, 104 may also occur automatically after the waste material has been drained from the waste containers 102, 104.

During operation of the cleaning system 400, once the waste containers 102, 104 are emptied, the main controller 130 instructs the docking controller to open a water valve 500 to allow water to flow from a pressurized water source through a main water line 504 in the docking station 101. The main controller 130 also instructs the docking controller to inject cleaner from a container 502 into the water line 504 via an injector 506 coupled to a cleaner line 507. The water with cleaner then flows through a water coupling 508 of the docking station 101 and the water coupling 406 of the waste collection unit 100 to the upper and lower supply lines 410, 412. The main controller 130 then opens the upper solenoid valve 414 to allow the water with cleaner to flow through the upper supply line 410 to the liquid delivery devices 430, 432 in the upper waste container 102 to spray the water with cleaner, under pressure, into the upper waste container 102. The main controller 130 then sends a command signal to the actuator 470 for the upper waste container 102 to rotate the liquid delivery devices 430, 432 in accordance with predefined operational parameters and sequences.

After the water with cleaner is sprayed in the upper waste container 102 for a predetermined period of time, the main controller 130 closes the upper solenoid valve 414 and opens the lower solenoid valve 416 to repeat the process for the lower waste container 104. In some instances, when there is enough water pressure present, both solenoid valves 414, 416 can be opened to clean both of the waste containers 102, 104 at the same time. After both the upper and lower waste containers 102, 104 have been cleaned, cleaner is no longer injected into the water line 504 and water without cleaner flows through the cleaning system 400 in a similar operation to rinse the upper and lower waste containers 102, 104. When “normal clean” or “extended clean” options are selected, these clean/rinse cycles could be repeated two or more times.

It should be appreciated that several different combinations of clean/rinse cycles, clean/rinse times, cleaner concentration, water flow, and the like could provide unlimited options.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

Exemplary Clauses

Clause 1—A waste collection unit for collecting waste material through a suction line during a medical procedure, the waste collection unit comprising: a waste container configured to be in fluid communication with the suction line to collect the waste material during the medical procedure, the waste container defining a collection chamber and a vacuum port; a vacuum source in selective communication with the vacuum port of the waste container for providing a vacuum in the waste container to draw the waste material into the waste container through the suction line, the vacuum source defining a vacuum passage to carry air through the vacuum source wherein the vacuum passage has a vacuum inlet for receiving the air and a vacuum outlet for directing the air from the vacuum source; and a sound attenuating enclosure in which the vacuum source is disposed, the sound attenuating enclosure defining an enclosure inlet for receiving cooling air to cool the vacuum source and an enclosure outlet for discharging warmed cooling air from the sound attenuating enclosure, wherein the sound attenuating enclosure comprises a first section at least partially formed of a first sound-absorbing material configured to attenuate noise generated by the vacuum source during operation, the first section having an interior surface with geometric features formed therein to accommodate the vacuum source and define a cooling air path for the cooling air.

Clause 2—The waste collection unit of clause 1, wherein the vacuum source comprises a vacuum pump.

Clause 3—The waste collection unit of clause 2, wherein the sound attenuating enclosure substantially surrounds the vacuum pump.

Clause 4—The waste collection unit of clause 2, wherein the geometric features comprise one or more of a pocket in the interior surface for receiving a portion of the vacuum pump, a seat against which the vacuum pump abuts, a recess, or a slot.

Clause 5—The waste collection unit of clause 4, wherein the first section is formed of the first sound-absorbing material and a noise barrier.

Clause 6—The waste collection unit of clause 4, wherein the first section comprises a noise barrier embedded in the first sound-absorbing material.

Clause 7—The waste collection unit of clause 6, wherein the first sound-absorbing material is molded around the noise barrier.

Clause 8, the waste collection unit of clause 7, wherein the noise barrier comprises at least one of metal and plastic.

Clause 9—The waste collection unit of any of clauses 5-8, wherein the noise barrier is flexible.

Clause 10—The waste collection unit of any of clauses 5-8, wherein the noise barrier is rigid.

Clause 11—The waste collection unit of clause 2, wherein the first section comprises one of a top section, a bottom section, a front section, a rear section, a right side section, and a left side section.

Clause 12—The waste collection unit of clause 11, wherein the side sections are at least partially formed of the first sound-absorbing material.

Clause 13—The waste collection unit of any of clauses 11 or 12, wherein the front section and the side sections comprise an integrally formed foam piece.

Clause 14—The waste collection unit of any of clauses 11-13, wherein the front section and the side sections have interior surfaces shaped to generally conform to a shape of the vacuum pump.

Clause 15—The waste collection unit of any of clauses 11-14, wherein at least one of the front section and the side sections include an integral flange formed of the first sound-absorbing material and compressed between metal portions of the sound attenuating enclosure.

Clause 16—The waste collection unit of any of clauses 11-15, wherein the bottom section supports the pump.

Clause 17—The waste collection unit of any of clauses 11-16, wherein one of the sections is at least partially formed of a second sound-absorbing material.

Clause 18—The waste collection unit of clause 17, wherein the first sound-absorbing material and the second sound-absorbing material are different.

Clause 19—The waste collection unit of any of clauses 11-18, wherein the sound attenuating enclosure engages the vacuum pump at a first location and is spaced from the vacuum pump at a second location to define the cooling air path for the cooling air.

Clause 20—The waste collection unit of clause 19, wherein the vacuum pump comprises a casing defining a casing inlet and a casing outlet, the vacuum pump further comprising a fan for drawing the cooling air into the casing at the casing inlet and exhausting the warmed cooling air from the casing outlet, wherein sound attenuating enclosure engages the vacuum pump at the first location to provide an air flow barrier outside the casing to limit the warmed cooling air from entering the casing inlet.

Clause 21—The waste collection unit of any of clauses 19 or 20, comprising a cooling air fan for providing the cooling air in the cooling air path.

Clause 22—The waste collection unit of any of the preceding clauses, comprising a plenum attached to the sound attenuating enclosure and defining a plenum chamber to collect the cooling air discharged from the enclosure outlet and the air from the vacuum outlet.

Clause 23—The waste collection unit of clause 22, wherein the vacuum source defines an exhaust passage and a muffler disposed between the vacuum outlet and the exhaust passage wherein the plenum chamber is arranged to collect the air from the exhaust passage.

Clause 24—The waste collection unit of clause 23, wherein the vacuum source defines second exhaust passage extending from the muffler wherein the plenum chamber is arranged to collect the air from both of the exhaust passages.

Clause 25—The waste collection unit of clause 23, comprising a check valve in the exhaust passage.

Clause 26—The waste collection unit of any of clauses 22-25, wherein the plenum defines a plenum inlet and a plenum outlet and the chamber has a tortuous path between the plenum inlet and the plenum outlet.

Clause 27—The waste collection unit of any of clauses 22-26, wherein the plenum is at least partially formed of a second sound-absorbing material to attenuate noise.

Clause 28—The waste collection unit of any of clauses 22-27, wherein the plenum comprises a plurality of sound absorbing projections.

Clause 29—The waste collection unit of clause 28, wherein the sound absorbing projections comprise one or more of acoustic cones, acoustic pyramids, or acoustic triangular ridges.

Clause 30—The waste collection unit of any of the preceding clauses, comprising a portable cart supporting the waste container and the vacuum source.

Clause 31—The waste collection unit of clause 1, wherein the first sound-absorbing material comprises thermoset foam.

Clause 32—The waste collection unit of clause 1, wherein the first sound-absorbing material comprises a thermoset polyurethane foam.

Clause 33—The waste collection unit of clause 32, wherein the thermoset polyurethane foam is a high density foam.

Clause 34—The waste collection unit of clause 1, wherein the first sound-absorbing material comprises closed cell foam.

Clause 35—The waste collection unit of clause 1, wherein the first sound-absorbing material comprises polyurethane foam with an additive.

Clause 36—A smoke evacuation system for evacuating smoke through a smoke conduit during a medical procedure, the smoke evacuation system comprising: a filter housing for removably receiving a filter; a smoke evacuator configured to draw the smoke from the smoke conduit into the filter housing and through the filter; and a sound attenuating enclosure in which the smoke evacuator is disposed, the sound attenuating enclosure defining an enclosure inlet for receiving filtered air from the filter housing and an enclosure outlet to direct the filtered air out of the sound attenuating enclosure, wherein the sound attenuating enclosure comprises a first section at least partially formed of a first sound-absorbing material configured to attenuate noise generated by the smoke evacuator during operation and the sound attenuating enclosure further defines a cooling air inlet for receiving cooling air, the first section having an interior surface with geometric features formed therein to accommodate the smoke evacuator and define a cooling air path for the cooling air.

Clause 37—The smoke evacuation system of clause 36, wherein the smoke evacuator comprises a motor.

Clause 38—The smoke evacuation system of clause 37, wherein the sound attenuating enclosure substantially surrounds the motor.

Clause 39—The smoke evacuation system of any of clauses 37 or 38, wherein the geometric features comprise one or more of a pocket for receiving the smoke evacuator, a seat for abutting the smoke evacuator, an annular rib for engaging the smoke evacuator, a recess, or a slot.

Clause 40—The smoke evacuation system of clause 39, wherein the first section is completely formed of the first sound-absorbing material.

Clause 41—The smoke evacuation system of clause 36, wherein the first section comprises a noise barrier embedded in the first sound-absorbing material.

Clause 42—The smoke evacuation system of clause 41, wherein the first sound-absorbing material is molded around the noise barrier.

Clause 43—The smoke evacuation system of clauses 41 or 42, wherein the noise barrier comprises at least one of metal or plastic.

Clause 44—The smoke evacuation system of any of clauses 41-43, wherein the noise barrier is flexible.

Clause 45—The smoke evacuation system of any of clauses 41-43, wherein the noise barrier is rigid.

Clause 46—The smoke evacuation system of any of clauses 39-45, wherein the sound attenuating enclosure comprises a second section, wherein the second section is formed of the first sound-absorbing material.

Clause 47—The smoke evacuation system of clause 46, wherein the first section and the second section are separate sections fixed together.

Clause 48—The smoke evacuation system of clauses 46 or 47, wherein the first section has an interior surface shaped to generally conform to a shape of the motor.

Clause 49—The smoke evacuation system of any of clauses 46-48, wherein the second section defines an air flow chamber.

Clause 50—The smoke evacuation system of any of clauses 36-49, comprising a plenum defining a plenum inlet and a plenum outlet, the enclosure outlet in fluid communication with the plenum inlet and the plenum defining a plenum chamber to collect the filtered air from the enclosure outlet.

Clause 51—The smoke evacuation system of clause 50, wherein the plenum is at least partially formed of a second sound-absorbing material to attenuate noise.

Clause 52—The smoke evacuation system of any of clauses 36-51, comprising a portable cart supporting the filter housing and the smoke evacuator.

Clause 53—The smoke evacuation system of any of clauses 36-52, wherein the first sound-absorbing material comprises a foam material.

Clause 54—The smoke evacuation system of clause 53, wherein the foam material comprises a thermoset polyurethane foam.

Clause 55—The smoke evacuation system of clause 54, wherein the thermoset polyurethane foam is a high density foam.

Clause 56—The smoke evacuation system of any of clauses 53-55, wherein the foam material comprises closed cell foam.

Clause 57—The smoke evacuation system of any of clauses 53-56, wherein the foam material comprises polyurethane foam with an additive.

Clause 58—A waste collection unit for collecting waste material through a suction line during a medical procedure, the waste collection unit comprising: a waste container configured to be in fluid communication with the suction line to collect the waste material during the medical procedure, the waste container having an internal surface defining a collection chamber; a vacuum source in selective communication with the waste container for providing a vacuum in the waste container to draw the waste material into the waste container through the suction line; and a cleaning system including a liquid delivery device rotatably supported relative to the waste container, the liquid delivery device configured to direct liquid on the internal surface, wherein the cleaning system includes an actuator operatively coupled to the liquid delivery device for rotating the liquid delivery device relative to the waste container to vary a direction in which the liquid is directed on the internal surface.

Clause 59—The waste collection unit of clause 58, wherein the cleaning system includes a second liquid delivery device with the actuator operatively coupled to each of the liquid delivery devices.

Clause 60—The waste collection unit of clause 59, wherein each of the liquid delivery devices comprises a spray nozzle.

Clause 61—The waste collection unit of clause 60, wherein the spray nozzles are replaceable.

Clause 62—The waste collection unit of clause 60 or 61, wherein each of the spray nozzles are configured to provide a spray pattern with a spray angle subtended by the spray pattern of at least eighty degrees.

Clause 63—The waste collection unit of any of clauses 60-62, wherein each of the spray nozzles are configured to discharge a flat spray pattern.

Clause 64—The waste collection unit of any of clauses 60-63, wherein the spray nozzles are configured to discharge spray patterns that impact the internal surface at different locations.

Clause 65—The waste collection unit of clause 64, wherein a first of the spray nozzles is configured to discharge a first spray pattern at an upper portion of the internal surface and a second of the spray nozzles is configured to discharge a second spray pattern at a lower portion of the internal surface.

Clause 66—The waste collection unit of any of clauses 59-65, wherein the actuator comprises a motor.

Clause 67—The waste collection unit of clause 66, wherein the motor is variable speed.

Clause 68—The waste collection unit of clauses 66 or 67, comprising a current sensor in communication with the motor for monitoring current drawn by the motor and detecting whether the motor is in a stalled condition.

Clause 69—The waste collection unit of any of clauses 59-68, wherein the cleaning system comprises a gear arrangement operatively coupling the actuator to the liquid delivery devices so that the liquid delivery devices rotate at different rotational speeds.

Clause 70—The waste collection unit of any of clauses 59-69, comprising a cap coupled to the waste container wherein the liquid delivery devices and the actuator are supported by the cap.

Clause 71—The waste collection unit of any of clauses 59-70, wherein the cleaning system comprises a manifold directing the liquid from a liquid source to the liquid delivery devices, the manifold comprising an inlet for receiving the liquid from the liquid source, a pair of openings through which the liquid enters the liquid delivery devices, and a main flow passage to carry the liquid from the inlet to the openings.

Clause 72—The waste collection unit of clause 71, wherein the cleaning system comprises a check valve disposed in the main flow passage to separate the openings.

Clause 73—The waste collection unit of clause 72, wherein the cleaning system comprises a prefill port in communication with the main flow passage to receive prefill liquid from a prefill liquid source, the check valve located so that the prefill liquid is unable to pass through both of the openings into both of the liquid delivery devices.

Clause 74—The waste collection unit of any of clauses 58-73, comprising a portable cart supporting the waste container, the vacuum source, and the cleaning system.

The invention claimed is:

1. A waste collection unit for collecting waste material through a suction line during a medical procedure, the waste collection unit comprising:

a waste container configured to be in fluid communication with the suction line to collect the waste material during the medical procedure, the waste container defining a collection chamber and a vacuum port;

a sound attenuating enclosure defining an enclosure inlet for receiving cooling air and an enclosure outlet, wherein the sound attenuating enclosure is at least partially formed of a sound-absorbing material configured to attenuate noise; and a vacuum source disposed in the sound attenuating enclosure and in selective communication with the vacuum port of the waste container for providing a vacuum in the waste container to draw the waste material into the waste container through the suction line, wherein the vacuum source comprises a casing defining a casing inlet at a first end of the vacuum source, a casing outlet, a fan for drawing the cooling air into the casing inlet and discharging warmed cooling air from the casing outlet, and a vacuum inlet for receiving working air and a vacuum outlet for discharging the working air, wherein the sound-absorbing material comprises a foam material forming:

a first end portion defining a first pocket that engages the casing at a first end of the vacuum source, wherein a bottom portion of the first pocket defines a seat configured to attenuate noise while providing a cooling air barrier that prevents the working air from circulating towards the casing inlet and the warmed cooling air from recirculating towards the casing inlet, wherein an upper portion of the first pocket opposite the seat is open from above and spaced apart from the casing inlet to provide an air path for a portion the cooling air to be drawn from the enclosure inlet to the casing inlet; and a second end portion defining a second pocket receiving a second end of the vacuum source, wherein the second pocket is sized to permit another portion of the cooling air to circulate around the vacuum source to be combined with the working air downstream of the vacuum source to be discharged through the enclosure outlet.

2. The waste collection unit of claim 1, wherein the seat extends around a bottom half of the first end of the vacuum source.

3. The waste collection unit of claim 1, further comprising a plenum attached to the sound attenuating enclosure and defining a plenum inlet aligned with the enclosure outlet, and a plenum chamber for collecting the warmed cooling air discharged from the enclosure outlet and the working air from the casing outlet.

4. The waste collection unit of claim 3, wherein the vacuum source defines an exhaust passage and comprises an exhaust hose disposed between the vacuum outlet and the exhaust passage, and wherein the plenum chamber is arranged to collect the air from the exhaust passage to be combined with the warmed cooling air from the enclosure outlet.

5. The waste collection unit of claim 1, wherein the sound attenuating enclosure further comprises a noise barrier, wherein the noise barrier is embedded in the sound-absorbing material.

6. The waste collection unit of claim 1, wherein the sound attenuating enclosure further comprises an integral flange formed of the sound-absorbing material and compressed between metal portions of the sound attenuating enclosure.

7. The waste collection unit of claim 1, wherein the foam material further forms a side portion extending between the first and second end portions defining an arcuate recess to provide the air path for the cooling air to be directed from the enclosure inlet to the upper portion of the first pocket.

8. A waste collection unit for collecting waste material through a suction line during a medical procedure, the waste collection unit comprising:

a waste container configured to be in fluid communication with the suction line to collect the waste material during the medical procedure, the waste container defining a collection chamber and a vacuum port;

a sound attenuating enclosure defining an enclosure inlet for receiving cooling air and an enclosure outlet, wherein the sound attenuating enclosure is at least partially formed of a sound-absorbing material configured to attenuate noise, wherein the sound-absorbing material comprises foam material; and a vacuum source disposed in the sound attenuating enclosure and in selective communication with the vacuum port of the waste container for providing a vacuum in the waste container to draw the waste material into the waste container through the suction line, wherein the vacuum source comprises a casing defining a casing inlet at a first end of the vacuum source, a casing outlet, and a fan for drawing the cooling air into the casing inlet and discharging warmed cooling air from the casing outlet, and a vacuum inlet for receiving working air and a vacuum outlet for discharging the working air, wherein internal geometries of the foam material define a first pocket engaging a first end of the vacuum source and second pocket receiving a second end of the vacuum source such that a (i) first air path is defined from the enclosure inlet, between the casing of the vacuum source and an upper portion of the foam material forming the first pocket, through the casing inlet, through the casing outlet, to the enclosure outlet, and (ii) a second air path is defined from the enclosure inlet through a gap formed between the second pocket and the vacuum source to the enclosure outlet, wherein a bottom portion of the foam material forming the first pocket comprises a seat configured to prevent the working air from circulating towards the casing inlet and the second air path from passing through the vacuum source so as to cool the vacuum source and the warmed cooling air being discharged from the vacuum source.

9. The waste collection unit of claim 8, wherein the foam material defines the first pocket receiving the first end of the vacuum source, and the second pocket receiving a second end of the vacuum source, wherein the first pocket further defines the first air path and the second pocket further defines the second air path.

10. The waste collection unit of claim 8, wherein the first air path and the second air path rejoin near the enclosure outlet.

11. The waste collection unit of claim 8, further comprising a plenum attached to the sound attenuating enclosure and defining a plenum inlet aligned with the enclosure outlet, and a plenum chamber for collecting the warmed cooling air discharged through the enclosure outlet from the first air path and the second air path.

12. A waste collection unit for collecting waste material through a suction line during a medical procedure, the waste collection unit comprising:

a cart base;

a plurality of wheels supporting the cart base;

a waste container configured to be in fluid communication with the suction line to collect the waste material during the medical procedure, the waste container defining a collection chamber and a vacuum port;

a sound attenuating enclosure comprising a top section defining an enclosure inlet for receiving cooling air, and a bottom section defining an enclosure outlet for discharging warmed cooling air from the sound attenuating enclosure, wherein the sound attenuating enclosure is at least partially formed of a sound-absorbing material configured to attenuate noise;

a vacuum source disposed in the sound attenuating enclosure and in selective communication with the vacuum port of the waste container for providing a vacuum in the waste container to draw the waste material into the waste container through the suction line, the vacuum source defining a vacuum inlet for receiving the cooling air and a vacuum outlet for discharging warmed cooling air; and a plenum comprising an outer noise barrier, and at least one foam piece lining walls of the outer noise barrier, wherein an upper edge of the outer noise barrier is attached to an exterior of the bottom section of the sound attenuating enclosure and positioned beneath the cart base wherein an upper surface of the at least one foam piece defines a plenum inlet aligned with the enclosure outlet, a plenum chamber defining a tortuous path configured to collect the warmed cooling air discharged from the enclosure outlet, and a plenum outlet, wherein one of the walls of the outer noise barrier defines an opening sized to and aligned with the plenum outlet of the at least foam piece such that the warmed cooling air discharged downwardly through the enclosure outlet is redirected to be discharged from the plenum outlet and upwardly away from beneath the cart base to avoid the warmed cooling air from being routed back into the enclosure inlet of the sound attenuating enclosure.

13. The waste collection unit of claim 12, wherein the vacuum source defines an exhaust passage and comprises a muffler disposed between the vacuum outlet and the exhaust passage, and wherein the plenum chamber is arranged to collect the air from the exhaust passage.

14. The waste collection unit of claim 12, wherein the plenum further comprises an outer noise barrier formed from a rigid material configured to reflect sound waves, and wherein the at least one piece of foam is disposed within and lining the outer noise barrier.

15. The waste collection unit of claim 12, wherein the plenum chamber is greater in size than the enclosure outlet such that the warmed cooling air expands to reduce sound energy.

16. The waste collection unit of claim 12, wherein the plenum outlet is further arranged to exhaust the warmed cooling air between a front pair or a rear pair of the wheels.

* * * * *